(12) United States Patent
Cha et al.

(10) Patent No.: US 9,051,586 B2
(45) Date of Patent: Jun. 9, 2015

(54) METHOD FOR CONVERTING AND PRODUCING CARBONATE MINERALS FROM CARBON DIOXIDE USING RECOMBINANT BIOCATALYST

(75) Inventors: Hyung Joon Cha, Pohang-si (KR); Im Gyu Kim, Pohang-si (KR); Dong Gyun Kang, Gangneung-si (KR); Byung Hoon Jo, Seongnam-si (KR); Jeong Hyun Seo, Pohang-si (KR)

(73) Assignee: POSTECH ACADEMY-INDUSTRY FOUNDATION, Pohang (KR)

( * ) Notice: Subject to any disclaimer, the term of this patent is extended or adjusted under 35 U.S.C. 154(b) by 61 days.

(21) Appl. No.: 13/817,468

(22) PCT Filed: Apr. 13, 2012

(86) PCT No.: PCT/KR2012/002816
§ 371 (c)(1),
(2), (4) Date: Feb. 18, 2013

(87) PCT Pub. No.: WO2013/002481
PCT Pub. Date: Jan. 3, 2013

(65) Prior Publication Data
US 2014/0113339 A1    Apr. 24, 2014

(30) Foreign Application Priority Data

Jun. 29, 2011    (KR) .................. 10-2011-0063729
Mar. 7, 2012    (KR) .................. 10-2012-0023429

(51) Int. Cl.
| | | |
|---|---|---|
| C12P 9/00 | (2006.01) | |
| C12P 7/00 | (2006.01) | |
| C12P 7/62 | (2006.01) | |
| C12N 9/88 | (2006.01) | |
| C12N 1/20 | (2006.01) | |
| A61L 9/01 | (2006.01) | |
| C12P 21/06 | (2006.01) | |
| C12P 19/34 | (2006.01) | |
| C07H 21/04 | (2006.01) | |
| C07K 1/00 | (2006.01) | |
| C12P 3/00 | (2006.01) | |

(52) U.S. Cl.
CPC ... *C12P 9/00* (2013.01); *C12N 9/88* (2013.01); *C12P 3/00* (2013.01)

(58) Field of Classification Search
CPC ............................................ C12N 9/88
USPC ......... 435/131, 132, 135, 232, 252.3, 252.33, 435/266, 69.1, 91.1; 536/23.1, 23.2; 530/350
See application file for complete search history.

(56) References Cited

U.S. PATENT DOCUMENTS

2010/0209997 A1*    8/2010    Newman et al. .............. 435/232

FOREIGN PATENT DOCUMENTS

| WO | 2009/021548 A1 | 2/2009 |
|---|---|---|
| WO | 2010/061185 A2 | 6/2010 |

OTHER PUBLICATIONS

Geers et al., Carbon Dioxide Transport and Carbonic Anhydrase in Blood and Muscles. Physiological reviews. 80: 681-715, 2000.*
Witkowski et al., Conversion of a β-Ketoacyl Synthase to a Malonyl Decarboxylase by Replacement of the Active-Site Cysteine with Glutamine. Biochemistry 38:11643-11650, 1999.*
Seffernick et al., Melamine Deaminase and Atrazine Chlorohydrolase: 98 Percent Identical but Functionally Different. J. Bacteriol. 183(8):2405-2410, 2001.*
Chirica et al., The complete sequence, expression in *Escherichia coli*, purification and some properties of carbonic anhydrase from *Neisseria gonorrhoeae*. Eur. J. Biochem.144. 755-760, 1997.*
Li et al., Functional Display of Foreign Protein on Surface of *Escherichia coli* Using N-Terminal Domain of Ice Nucleation Protein. Biotechnology and Bioengineering.vol. 85, No. 2, 2004.*
Paul K. Addo, et al., "Mathanol Production via bioelectrocatalytic Reduction of Carbon Dioxide: Role of Carbonic Anhydrase in Improving Electrode Performance", Electrochemical and Solid-State Letters, vol. 14(4), pp. E9-E13, Feb. 15, 2011.
Im Gyu Kim, et al., "Investigation on carbonic anhydrase for carbon dioxide sequestration and subsequent conversion to calcium carbonate", The Korean Society for Biotechnology and Bioengineering Spring Meeting, p. 125 (PSP29) presented on: Apr. 14-16, 2011.
Hyung Joon Cha, et al, "Conversion of carbon dioxide to chemical using biocatalyst", CCS Conference, 1st Korea Carbon Capture & Sequestration (CCS) Conference, presented on: Apr. 13-15, 2011.
Parissa Mirjafari, et al., "Investigating the Application of Enzyme Carbonic Anhydrase for CO2 Sequestration Purposes", Industrial & Engineering Chemistry Research, vol. 46, No. 3, Jan. 1, 2007, pp. 921-926.

(Continued)

*Primary Examiner* — Ganapathirama Raghu
(74) *Attorney, Agent, or Firm* — Lexyoume IP Meister, PLLC

(57) ABSTRACT

The present invention relates to a technique for capturing carbon dioxide and converting the carbon dioxide to carbonate minerals using a recombinant whole cell biocatalyst expressing carbonic anhydrase. More particularly, the present invention relates to a composition for capturing carbon dioxide and a method for capturing carbon dioxide using the composition, which composition comprises a whole cell of a transformant formed with a vector including a nucleic acid encoding a recombinant carbonic anhydrase; a cell lysate or its fraction of the whole cell; or a recombinant carbonic anhydrase isolated from the whole cell. Further, the present invention relates to a composition and method for converting the carbon dioxide to carbonate minerals using the carbon dioxide capturing composition.

14 Claims, 13 Drawing Sheets
(11 of 13 Drawing Sheet(s) Filed in Color)

(56) References Cited

OTHER PUBLICATIONS

Favre N, et al., "Biocatalytic capture of CO2 with carbonic anhydrase and its transformation to solid carbonate", Journal of Molecular Catalysis B: Enzymatic, Elsevier, Amsterdam, NL, vol. 60, No. 3-4, Oct. 1, 2009, pp. 163-170.

Im Gyu Kim, et al., "Biomineralization-based conversion of carbon dioxide to calcium carbonate using recombinant carbonic anhydrase", Chemosphere, vol. 87, No. 10, Jun. 1, 2012, pp. 1091-1096.

Kaneko T et al. Database UniProt [online], Accession No. F7UQC7, <URL: http://www.uniprot.org/uniprot/F7UQC7.txt?version=6>, Feb. 22, 2012 uploaded, [retrieved on Aug. 25, 2014], Definition: RecName: Full=Carbonic anhydrase; EC=4.2.1.1.

Heung-Chae Jung, et al., "Expression of carboxymethylcellulase on the surface of *Escherichia coli* using *Pseudomonas syringae* ice nucleation protein", Enzyme Microb. Technol., Apr. 1998, vol. 22, pp. 348-354.

Shenghua Huang, et al., "Crystal Structure of Carbonic Anhydrase from *Neisseria gonorrhoeae* and its Complex with the Inhibitor Acetazolamide", J. Mol. Biol., Oct. 16, 1998, vol. 283, pp. 301-310.

EPO, extended European Search Report dated Jul. 21, 2014, of the corresponding European Patent Application No. 12804123.3.

\* cited by examiner

|  | BCA | NCA | S | W |
|---|---|---|---|---|
| Time(s) | 0.7 | 0.98 | 2.25 | 2.75 |
| Activity (U/mg) | 3090 | 2184 | 920 | 728 |

< BCA >

<PURIFIED FRACTION>

<SOLUBLE FRACTION>

<WHOLE CELL>

< BSA >

METHOD FOR CONVERTING AND PRODUCING CARBONATE MINERALS FROM CARBON DIOXIDE USING RECOMBINANT BIOCATALYST

TECHNICAL FIELD

The present invention relates to a technique for capturing carbon dioxide and converting the carbon dioxide to carbonate minerals using a recombinant whole cell biocatalyst expressing carbonic anhydrase. More particularly, the present invention relates to a composition for capturing carbon dioxide ($CO_2$) and a method for capturing carbon dioxide using the composition, which comprises: a recombinant whole cell transformed with a vector containing a nucleic acid encoding a carbonic anhydrase to express a carbonic anhydrase in cytoplasm, periplasmic space, or cell surface; a cell lysate or its fraction of the whole cell; or a recombinant carbonic anhydrase isolated from the whole cell. Further, the present invention relates to a composition and method for converting the carbon dioxide to carbonate minerals using the composition for capturing carbon dioxide.

BACKGROUND ART

There have been increasing worldwide attempts to reduce the concentration of carbon dioxide ($CO_2$) in the atmosphere in association with the global warming issue. The establishment of techniques for reducing carbon dioxide is necessary in consideration of the current situation that the use of fossil energy is going to be inevitable in near future in spite of the ongoing development of renewable energy. A variety of chemical and physical methods for absorption of carbon dioxide have been developed and mostly encounter problems related to high heat recovery, corrosion, additional storage space, and so forth. Recently, attractions have been drawn by a method for a biological capture of carbon dioxide ($CO_2$) with an enzyme involved in biological $CO_2$ fixation. Such a method for biological $CO_2$ capture is of great benefit in the aspects of eco-friendliness, rapid reaction, and above all, conversion of carbon dioxide to the final compound, more advantageous over the conventional chemical and physical methods.

Carbonic anhydrase is a Zn-containing metalloenzyme that is known to exist in tissues of mammals, plants, or green algae and catalyze the hydration of carbon dioxide. Up to date, the carbonic anhydrase has been classified into five categories according to sequence similarity: $\alpha$, $\beta$, $\gamma$, $\delta$, and $\epsilon$. For example, $\alpha$-carbonic anhydrase is the type to be found in most of mammals, and part of bacteria and green algae; $\beta$-carbonic anhydrase is present in most of prokaryotes and plants; $\gamma$-carbonic anhydrase is found in methane-producing bacteria, *Methanosarcina thermophilia*; $\delta$-carbonic anhydrase is a recently reported carbonic anhydrase found in diatoms; and $\epsilon$-carbonic anhydrase is present in part of chemolithotrophs.

Carbon dioxide in atmosphere is dissolved in water to form a carbonate according to the following reactions. The carbonate exists in the form of carbonate ion ($CO_3^{2-}$), which reacts with a metal cation to form a precipitate.

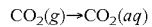

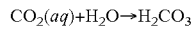

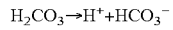

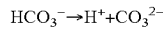

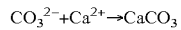

In the mechanism, the hydration reaction of carbon dioxide is the rate-determining step and accelerated in the presence of a carbonic anhydrase. Further, the final product obtained after catalyzing the capture of carbon dioxide is ready to react with different metal cations, such as calcium ion ($Ca^{2+}$), manganese ion ($Mn^{2+}$), iron ion ($Fe^{2+}$), etc., to form different carbonates, such as calcium carbonate ($CaCO_3$), manganese carbonate ($MnCO_3$), iron carbonate ($FeCO_3$), etc. These carbonates can be used in various industrial applications for different use purposes.

The presence of a carbonic anhydrase can accelerate the precipitation as well as the catalytic hydration of carbon dioxide. This is because the carbonic anhydrase catalyzes the hydration to promote the rate of forming carbonate ions, resulting in the faster precipitation of the carbonate.

Despite the catalytic function of carbonic anhydrase, the extraction of carbonic anhydrase from the nature for industrial use purposes has been limited due to the expense of enzyme purification and additional enzyme fixation. Bovine carbonic anhydrase extracted from bovine serum has been widely used, but its practical utilization is limited because it costs high as much as about three thousand dollars per gram. The techniques for extraction and purification of carbonic anhydrase from organisms have been developed incompletely, and the genetically recombinant carbonic anhydrase has been studied only for the biochemical research on enzymes. However, there have ever been yet made attempts neither to convert carbon dioxide to carbonates using a recombinant carbonic anhydrase which can be produced in large scale, nor to utilize a recombinant whole cell as a catalyst.

In an attempt to develop a technique for conversion of carbon dioxide to carbonates using a carbonic anhydrase with high efficiency at low cost, the inventors of the present invention have contrived a recombinant carbonic anhydrase available in practical use and a recombinant whole cell biocatalyst using transformant cells expressing the recombinant carbonic anhydrase in large scale. To complete the present invention, the inventors prepared a vector including a carbonic anhydrase gene and successfully expressed the vector in *Escherichia coli* in large scale. They also demonstrated that both the recombinant carbonic anhydrase produced from the vector and the whole cell biocatalyst expressing a carbonic anhydrase had high activity on the hydration of carbon dioxide, and the use of recombinant carbonic anhydrase contributed to effective conversion of carbon dioxide to carbonate.

DISCLOSURE

Technical Problem

It is an object of the present invention to provide a composition for capturing carbon dioxide that comprises at least one selected from the group consisting of: a whole cell of a transformant formed with a vector including a nucleic acid encoding a carbonic anhydrase; a cell lysate or its fraction of the whole cell; and a carbonic anhydrase isolated from the whole cell.

It is another object of the present invention to provide a method for capturing carbon dioxide using the composition for capturing carbon dioxide.

It is still another object of the present invention to provide a composition for converting carbon dioxide to a carbonate or a bicarbonate that comprises the $CO_2$ capturing composition and a metal cation.

It is still further another object of the present invention to provide a method for converting carbon dioxide to a carbonate or a bicarbonate using the composition.

Technical Solution

In one preferred embodiment of the present invention to achieve the above objects, the present invention is directed to a composition for capturing carbon dioxide that comprises at least one selected from the group consisting of: a whole cell of a transformant formed with a vector including a nucleic acid encoding a recombinant carbonic anhydrase; a cell lysate or its fraction of the whole cell; or a carbonic anhydrase isolated from the whole cell.

The term "carbonic anhydrase (CA)" as used herein refers to a Zn-containing metallic enzyme that catalyzes the hydration of carbon dioxide ($CO_2(aq)+H_2O \rightarrow H^+ +HCO_3^-$). The bovine carbonic anhydrase derived from bovine serum as a conventional carbonic anhydrase for industrial use has been limited in its practical utilization due to the difficulty of purification and high expense of production. However, the present invention provides a carbonic anhydrase expressed in large scale by genetic recombination and useful as a whole cell catalyst to capture carbon dioxide and prepare carbonates from carbon dioxide with ease at low cost, with high catalytic activity equivalent to that of the conventional enzyme from bovine serum.

The present invention features a carbonic anhydrase expressed by genetic recombination. The carbonic anhydrase may be derived from any organism as long as it has a catalytic function on the hydration of carbon dioxide. For example, the carbonic anhydrase of the present invention can be derived from prokaryotes or eukaryotes and, more specifically from, if not limited to, gram-positive bacteria, gram-negative bacteria, bacteria, fungi, yeasts, plants, animals, or human.

Preferably, the carbonic anhydrase of the present invention may be derived from *Synechocystis* PCC6803, *Escherichia coli*, or *Neisseria gonorrhoeae* and expressed by genetic recombination. The growth of *Neisseria gonorrhoeae* is accelerated the presence of carbon dioxide. The carbonic anhydrase from *Neisseria gonorrhoeae* exists as a monomer and has a high $k_{cat}/K_M$ value approximating 46% with respect to human carbonic anhydrase II (HCA II) which is known to have the highest $k_{cat}/K_M$ value among the existing carbonic anhydrases, so that it can be readily secreted from the periplasmic space or cell surface to desirably enhance the catalytic efficiency. This example is given only to exemplify the present invention and not intended to limit the scope of the present invention.

Preferably, the carbonic anhydrase of the present invention may be used in the form of at least one selected from the group consisting of: a whole cell of a transformant formed with a vector including a nucleic acid encoding a carbonic anhydrase; a cell lysate or its fraction of the whole cell; and a carbonic anhydrase isolated from the whole cell. The fraction may include a soluble fraction, an insoluble fraction, a cytoplasmic fraction, a periplasmic fraction, or a cell membrane fraction of the cell lysate.

Preferably, the transformant cell may be expressed in cytoplasm, periplasmic space, or cell surface.

For this, as a preferred example, the carbonic anhydrase from *Neisseria gonorrhoeae* may be a protein having an amino acid sequence of SEQ ID NO: 1, which is expressed in cytoplasm. The nucleic acid encoding the carbonic anhydrase having an amino acid sequence of SEQ ID NO: 1 may have, if not specifically limited to, a nucleic acid sequence of SEQ ID NO: 2.

In the present invention, the carbonic anhydrase from *Neisseria gonorrhoeae* may also be a protein having an amino acid sequence of SEQ ID NO: 3 and produced in the periplasmic space, for the protein is formed by insertion of TorA as a signal sequence for inducing protein expression in *Escherichia coli* cytoplasm into the N-terminal domain of SEQ ID NO: 1. The nucleic acid encoding the carbonic anhydrase having an amino acid sequence of SEQ ID NO: 3 may have, if not specifically limited to, a nucleic acid sequence of SEQ ID NO: 4.

In the present invention, the carbonic anhydrase from *Neisseria gonorrhoeae* may also be a protein having an amino acid sequence of SEQ ID NO: 5 and produced in the cell surface, for the protein is formed by insertion of an ice nucleation protein sequence as a surface anchoring motif for secretion in *Escherichia coli* cell surface into the N-terminal domain of SEQ ID NO: 1. The nucleic acid encoding the carbonic anhydrase having an amino acid sequence of SEQ ID NO: 5 may have, if not specifically limited to, a nucleic acid sequence of SEQ ID NO: 6.

In the present invention, the carbonic anhydrase from *Synechocystis* may be a protein having an amino acid sequence of SEQ ID NO: 7, which protein is produced in the cytoplasm. The nucleic acid encoding the carbonic anhydrase having an amino acid sequence of SEQ ID NO: 7 may have, if not specifically limited to, a nucleic acid sequence of SEQ ID NO: 8.

In the present invention, the carbonic anhydrase may also be a protein having an amino acid sequence of SEQ ID NO: 9 and produced in the periplasmic space, for the protein is formed by insertion of TorA as a signal sequence for protein expression in the *Escherichia coli* periplasmic space into the N-terminal domain of SEQ ID NO: 7. The nucleic acid encoding the carbonic anhydrase having an amino acid sequence of SEQ ID NO: 9 may have, if not specifically limited to, a nucleic acid sequence of SEQ ID NO: 10.

In the present invention, the carbonic anhydrase from *Escherichia coli* may be a protein having an amino acid sequence of SEQ ID NO: 11 and produced in the cytoplasm. The nucleic acid encoding the carbonic anhydrase having an amino acid sequence of SEQ ID NO: 11 may have, if not specifically limited to, a nucleic acid sequence of SEQ ID NO: 12.

In the present invention, the carbonic anhydrase may also be a protein having an amino acid sequence of SEQ ID NO: 13 and produced in the periplasmic space, for the protein is formed by insertion of TorA as a signal sequence for protein expression in the *Escherichia coli* periplasmic space into the N-terminal domain of SEQ ID NO: 11. The nucleic acid encoding the carbonic anhydrase having an amino acid sequence of SEQ ID NO: 13 may have, if not specifically limited to, a nucleic acid sequence of SEQ ID NO: 14.

The genetic recombination process for producing the biocatalyst of the present invention includes the following steps.

The first step is preparing a vector including a nucleic acid encoding a carbonic anhydrase.

The nucleic acid encoding a carbonic anhydrase may be preferably derived from, for example, *Neisseria gonorrhoeae*, *Synechocystis*, or *Escherichia coli*, and appropriately modified by a known method to be expressed in a desired region of the host cell, such as cytoplasm, periplasmic space, or cell surface. More specifically, the nucleic acid may encode an amino acid sequence of SEQ ID NO: 1, SEQ ID NO: 3, SEQ ID NO: 5, SEQ ID NO: 7, SEQ ID NO: 9, SEQ ID NO: 11, or SEQ ID NO: 13, and have a nucleic acid sequence of SEQ ID NO: 2, SEQ ID NO: 4, SEQ ID NO: 6, SEQ ID NO: 8, SEQ ID NO: 10, SEQ ID NO: 12, or SEQ ID NO: 14.

The vector for inserting the nucleic acid may be a recombinant vector in different forms of plasmid, virus, cosmid. The term "recombinant vector" as used herein refers to a double-stranded DNA fraction as a carrier with a foreign DNA fraction. The term "foreign DNA" as used herein refers to a DNA originated from a foreign species, or otherwise, a substantially modified form of the original DNA fraction. The foreign gene encodes a polypeptide with a specific nucleic acid to be transcribed. According to the object of the present invention, the foreign DNA means a nucleic acid encoding a carbonic anhydrase.

To enhance the expression level of a transformed gene in a host cell, the recombinant vector has the target gene operatively linked to a transcription/decoding/expression control sequence in the selected host cell. The recombinant vector is a gene construct which contains a necessary control factor operatively linked to express an inserted gene fraction in the target cell. The standard recombinant DNA technique is used to produce such a gene construct. The recombinant vector is not specifically limited as long as it can express a target gene and produce a target protein in all kinds of host cells such as prokaryotes or eukaryotes. The preferred recombinant vector has a promoter excellent in activity and expression ability and capable of large-scale expression of a foreign protein similar to the natural form. Preferably, the recombinant vector may include at least a promoter, an initiation codon, a gene for encoding a target protein, a termination codon, and a terminator. In addition, the recombinant vector may appropriately include a DNA for encoding a signal peptide, an enhancer sequence, non-coding regions for the 5' and 3 termini of a target gene, a selectable marker region, or a replicable unit.

In the specified examples of the present invention, a vector was prepared so that a nucleic acid encoding carbonic anhydrase derived from *Neisseria gonorrhoeae*, *Synechocystis*, or *Escherichia coli* was inserted into a vector pET22b(+) or pTrcHis, which vector had a cleavage map of FIG. 1.

The second step is preparing a transformant cell using the vector including a nucleic acid encoding a carbonic anhydrase.

The method for preparing a transformant by introducing a recombinant vector into a host cell may a well-known method to introduce a nucleic acid into a cell, which method may include, if not specifically limited to, calcium phosphate- or calcium chloride/rubidium chloride-mediated transformation, elctroporation, electroinjection, heat shock transformation, chemical transformation using chemicals such as PEG, gene gun transformation, retroviral infection, microinjection, DEAE-dxtran transformation, cationic liposome transformation, or the like.

The host cell to be transformed with the recombinant vector of the present invention may be any prokaryote or eukaryote and required to have a high introduction efficiency of DNA and a high expression efficiency of the introduced DNA. The specific examples of the host cell may include known prokaryote or eukaryote cells, such as *Escherichia coli*, *Pseudomonas*, *Bacillus*, *Streptomyces*, Fungi, or yeasts; insect cells such as *Spodoptera Frugiperda* (SF9); animal cells, such as CHO, COS 1, COS 7, BSC 1, BSC 40, BMT 10, etc. Among these, *Escherichia coli* is preferred.

In the specified examples of the present invention, the vector, that is, an expression vector where a nucleic acid encoding a carbonic anhydrase was inserted in pET22b(+) or pTrcHis was introduced into *Escherichia coli* BL21 (DE3) through heat shock transformation at 42° C. for 2 minutes to prepare a transformant for large-scale production of carbonic anhydrase.

The third step is culturing the transformant to induce expression of carbonic anhydrase and accumulate the produced carbonic anhydrase.

The cultivation of the transformant expressing the recombinant vector in a nutrient medium can produce and isolate a useful protein in large scale. The medium and culture conditions are properly determined as accepted in the related art depending on to the type of the host cell. Such conditions as temperature, pH value of the medium, and culture time can be properly controlled to favor the growth of the cell and the large-scale production of the protein during the cultivation. IPTG (isopropyl-β-D-thiogalactopyranoside) is used as an expression-inducing factor to induce protein expression, and the induction time is controlled to maximize the yield of the protein.

In the specified examples of the present invention, the transformed *Escherichia coli* cells were cultured in a LB medium supplemented with ampicillin. When the absorbance ($OD_{600}$) of the culture sample at 600 nm reached 0.6 to 0.8, IPTG as a substance for inducing protein expression and $ZnSo_4$ for introducing zinc (Zn) were added to the culture sample, which were then cultured at 25° C. for more 25 hours. But, these culture conditions can be properly modified by those skilled in the art.

To investigate the expression of the carbonic anhydrase according to the above-described method, the transformant cell thus harvested is suspended with an aqueous buffer solution, crushed with a ultrasonic pulverizer and then partly separated into a soluble fraction and an insoluble fraction on a typical SDS-PAGE.

The transformant with the enzyme expressed is useful as a whole cell biocatalyst. More preferably, at least one selected from the group consisting of the transformant (whole cell), the lysate or its fraction of the transformant cell, and a carbonic anhydrase isolated from the transformant cell may be used as a biocatalyst.

In accordance with a preferred embodiment of the present invention, the recombinant carbonic anhydrase may be used as a whole cell biocatalyst produced in cytoplasm, periplasmic space, or cell surface without a process for separation and purification of carbonic anhydrase.

In accordance with another preferred embodiment of the present invention, the transformant cell expressing a carbonic anhydrase may be destroyed by different physical or chemical means, such as repetitive freeze-thawing, ultrasonic waves, mechanical destruction, or cell-degrading agents. The cell lysate containing the destroyed cells may be directly used as a biocatalyst.

In accordance with still another preferred embodiment of the present invention, the cell lysate containing the destroyed cells may be separated into a soluble fraction and an insoluble fraction, both of which are useful as a biocatalyst. Further, a cytoplasm fraction, a periplasmic fraction, or a cell membrane fraction may also be used as a biocatalyst.

In accordance with still another preferred embodiment of the present invention, the carbonic anhydrase produced in the transformant cell may be used as a biocatalyst after isolation and purification. The carbonic anhydrase thus produced can be isolated and purified by known biochemical isolation techniques after pulverization of the transformant cell. For example, the isolation and purification methods may include, if not specifically limited to, electrophoresis, centrifugal separation, gel filtration, precipitation, dialysis, chromatography (ion-exchange chromatography, affinity chromatography, immune-affinity chromatography, reverse HPLC, gel permeation HPLC, etc.), isoelectric focusing, or various modifications or combinations of these methods.

In a specified example of the present invention, to obtain a carbonic anhydrase derived from *Neisseria gonorrhoeae*, the transformant cells harvested were destroyed with an ultrasonic pulverizer, and the soluble fraction of the cell lysate was subjected to affinity chromatography using a column filled with a nickel resin to isolate and purify a desired carbonic anhydrase. The purified protein was removed of the salt (imidazole) remaining in the aqueous protein solution through dialysis using tris-sulfate (pH 7.6). The purification of the target carbonic anhydrase was investigated using SDS-PAGE and Western Blotting (See. FIG. 7).

In another specified example of the present invention, the purified enzyme was analyzed in regard to activity on hydration of carbon dioxide. Then, the whole cell and the soluble fraction obtained by destruction of the whole cell with an ultrasonic pulverizer were analyzed in regard to activity on hydration of carbon dioxide. The positive control was commercial bovine carbonic anhydrase extracted from bovine serum, and the negative control was bovine serum albumin inactive on the hydration of carbon dioxide. The results showed that all of the transformed whole cell, its soluble fraction, and the carbonic anhydrase isolated from the soluble fraction had such a high activity of capturing carbon dioxide as comparable to the positive control (See. FIG. 8).

In accordance with further another embodiment of the present invention, there is provided a method for capturing carbon dioxide using the composition for carbon dioxide.

More specifically, the present invention is directed to a method for capturing carbon dioxide that comprises: preparing the composition for capturing carbon dioxide; and feeding carbon dioxide into the composition for capturing carbon dioxide.

The preparation of the composition for capturing carbon dioxide may include: (1) preparing a vector including a nucleic acid encoding a carbonic anhydrase; (2) preparing a transformant cell formed with the vector; (3) culturing the transformant cell to induce expression of carbonic anhydrase and accumulate the carbonic anhydrase; and (4) preparing a composition including at least one selected from the group consisting of the transformant cell, a cell lysate or its fraction of the transformant cell, and the carbonic anhydrase isolated from the transformant cell.

The method of feeding carbon dioxide into the composition for capturing carbon dioxide may include, if not specifically limited to, feeding a source of carbon dioxide that contains a large amount of carbon dioxide and needs to be removed of carbon dioxide, such as in the form of waste water or flue gas.

After capturing carbon dioxide with the composition for capturing carbon dioxide according to the present invention, a source of metal cation is added to the composition to convert the captured carbon dioxide to a carbonate/bicarbonate precipitate, which is useful for industrial use purpose in various applications.

In accordance with still another embodiment of the present invention, there is provided a composition for converting carbon dioxide to a carbonate or a bicarbonate that comprises the composition for capturing carbon dioxide, and a metal cation.

According to the present invention, there is also provided a method for converting carbon dioxide to a carbonate or a bicarbonate using the composition.

Preferably, the present invention is directed to a method for converting carbon dioxide to a carbonate or a bicarbonate that includes: preparing the composition for capturing carbon dioxide; and feeding a metal cation and carbon dioxide into the composition for capturing carbon dioxide.

The term "carbonate" or "carbonate precipitate" as used herein refers to an inorganic component containing a carbonate group ($-CO_3$). This term may include both a mixture of carbonate and bicarbonate, and a species containing a carbonate ion alone. The term "bicarbonate" or "bicarbonate precipitate" as used herein refers to an inorganic component containing a bicarbonate group ($-HCO_3$). This term may include both a mixture of carbonate and bicarbonate, and a species containing a bicarbonate ion alone.

The source of metal ion that reacts with carbon dioxide to form a carbonate or a bicarbonate is not specifically limited as long as it contains a metal ion, and can be properly chosen according to its use. The preferred source of metal ion may react with the source of carbonate to produce a carbonate in a crystal form of calcite, aragonite or vaterite, or in an amorphous crystal form.

For example, the source of metal ion may be $Na^+$, $Ca^{2+}$, $Fe^{2+}$, $Mn^{2+}$, $Sr^{2+}$, $Ca^{2+}$, $Ba^{2+}$, $Zn^{2+}$, or $Pb^{2+}$, or its nitrate, hydrochloride, hydrate or alkaline solution.

The carbonate precipitate prepared with the source of metal ion may include, if not specifically limited to, sodium carbonate, calcium carbonate, iron carbonate, manganese carbonate, strontium carbonate, barium carbonate, zinc carbonate, or lead carbonate.

In the step of feeding a metal cation and carbon dioxide into the composition for capturing carbon dioxide according to the present invention, the metal cation and the carbon dioxide may be supplied in sequence or simultaneously. For example, the sequential feeding is conducted in the order of metal cation and carbon dioxide, or in the order of carbon dioxide and metal cation; otherwise, the simultaneous feeding of the metal cation and the carbon dioxide is conducted.

In a specified example of the present invention, calcium ions were fed into the carbon dioxide captured with the purified carbonic anhydrase of the present invention, the soluble fraction, and the whole cell. Then, the production of calcium carbonate was investigated with an X-ray diffractometer (XRD) and a scanning electron microscope (SEM) (See. FIGS. 11 and 12).

The carbonate or bicarbonate produced by reaction between carbon dioxide and a metal cation is useful in the industrial applications. For example, the carbonate or bicarbonate may be used as an inorganic filler in a wide range of industrial applications, such as rubber, plastic, paper, paint, coating, adhesive, cosmetics, medicine and medical supplies, and so forth.

Calcium carbonate is one of the minerals present in most quantity in the nature. Particularly, the calcium carbonate precipitate is an inorganic powder with an adequate specific gravity that is insoluble in pure water and characterized by high whiteness and non-inflammability, so that it can be used as an inorganic filler in a wide range of industrial applications. When used as a raw material, such as a filler for rubber, plastic, or paint, or a pigment for paper making, the aragonite-type calcium carbonate precipitate, which is of a needle-like shape with a considerably high aspect ratio (the ratio of crystal length to size), can enhance strength and whiteness and make opacity controllable due to its complicated needle-like surface structure, so that it is useful as an alternative as a novel functional inorganic powder capable of providing mechanical and optical functions. In this manner, the present invention can provide usefulness in producing calcium carbonate.

Advantageous Effects

The present invention is economically beneficial in that carbon dioxide can be captured using a supernatant liquid of the cell lysate or a transformant cell expressing carbonic anhydrase as a whole cell biocatalyst without a need of separately extracting the enzyme. Further, the final product is converted to a high value-added carbonate and thus can be utilized for various use purposes in the industrial applications, such as of paint, plastic, rubber, paper making, coating, adhesive, cosmetics, medicine and medical supplies, and so forth.

DESCRIPTION OF DRAWINGS

The file of this patent contains at least one drawing executed in color. Copies of this patent with color drawing(s) will be provided by the Patent and Trademark Office upon request and payment of the necessary fee.

MODE FOR INVENTION

Figure 1:
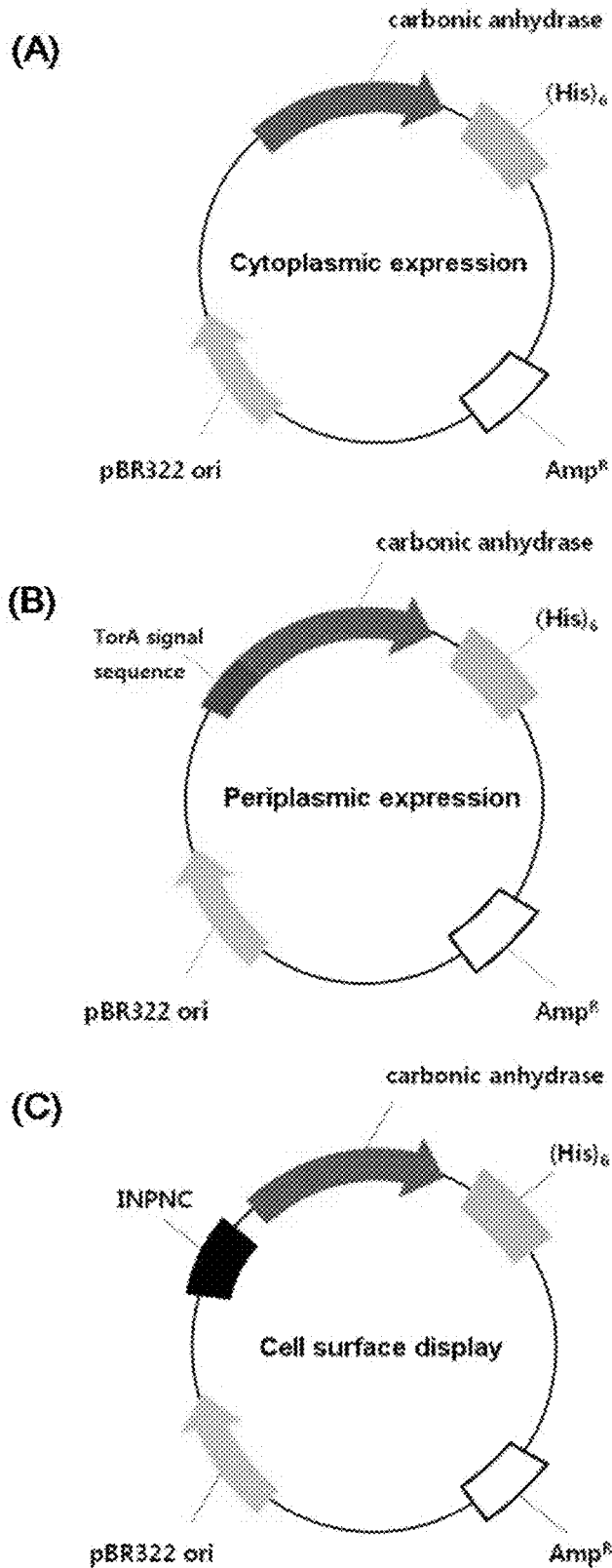
FIG. 1 shows cleavage maps of expression vectors containing a carbonic anhydrase gene: (A) a vector for cytoplasmic expression; (B) a vector for periplasmic expression; and (C) a vector for cell surface expression.

Hereinafter, the present invention will be described in detail with reference to examples, which are given only to exemplify the present invention and not intended to limit the scope of the present invention.

Example 1

Preparation of Carbonic Anhydrase Expression Vector 1-1. Preparation of Vector for Cytoplasmic Expression A carbonic anhydrase gene of *Neisseria gonorrhoeae* was amplified using two primers of a *Neisseria gonorrhoeae* genome DNA (i.e., forward primer: 5'-CATATGCACGGCAATCACACC-3' (SEQ ID NO: 15), and backward primer: 5'-AAGCTTTTCAATAACTACACGTGCATT-3' (SEQ ID NO: 16)), a Taq DNA polymerase, a dNTP mixed solution, and a PCR buffer by carrying out 30 cycles of PCR (30-sec denaturation at 95° C., 30-sec coupling at 55° C. and one-minute polymerization reaction at 72° C.) and then cooling down to 4° C. The carbonic anhydrase gene thus amplified was introduced into a pET-22b(+) vector using a NdeI/XhoI restriction enzyme to prepare a cytoplasmic expression vector for a carbonic anhydrase derived from *Neisseria gonorrhoeae*.

A carbonic anhydrase gene of *Synechocystis* was amplified using two primers of a *Synechocystis* genome DNA (i.e., forward primer: 5'-CATATGGCCGAAGTTTCATTGATATCC-3' (SEQ ID NO: 17), and backward primer: 5'-CAAGCTTACGGGAGCCTCGATAAATGCGC-3' (SEQ ID NO:18)), a Taq DNA polymerase, a dNTP mixed solution, and a PCR buffer by carrying out 30 cycles of PCR (30-sec denaturation at 95° C., 30-sec coupling at 55° C. and one-minute polymerization reaction at 72° C.) and then cooling down to 4° C. The carbonic anhydrase gene thus amplified was introduced into a TorA-GFP-removed pTTG vector (Korean Patent Application No. 2005-0099758) using a NdeI/HindIII restriction enzyme to prepare a cytoplasmic expression vector for a carbonic anhydrase derived from *Synechocystis*.

A carbonic anhydrase gene of *Escherichia coli* was amplified using two primers of a *Escherichia coli* genome DNA (i.e., forward primer: 5'-CATATGAAAGAGATTATTGATGGATTCC-3' (SEQ ID NO: 19), and backward primer: 5'-CAAGCTTCGCTGCGGTCGGTTGGCGTAG-3' (SEQ ID NO: 20)), a Taq DNA polymerase, a dNTP mixed solution, and a PCR buffer by carrying out 30 cycles of PCR (30-sec denaturation at 95° C., 30-sec coupling at 55° C. and one-minute polymerization reaction at 72° C.) and then cooling down to 4° C. The carbonic anhydrase gene thus amplified was introduced into a TorA-GFP-removed pTTG vector using a NdeI/HindIII restriction enzyme to prepare a cytoplasmic expression vector for a carbonic anhydrase derived from *Escherichia coli*.

1-2. Preparation of Vector for Periplasmic Expression

A carbonic anhydrase gene of *Neisseria gonorrhoeae* was amplified using two primers of a *Neisseria gonorrhoeae* genome DNA (i.e., forward primer: 5'-CCATGGGACACG-GCAATCACACC-3' (SEQ ID NO: 21), and backward primer: 5'-AAGCTTTTCAATAACTACACGTGCATT-3' (SEQ ID NO: 16)), a Taq DNA polymerase, a dNTP mixed solution, and a PCR buffer by carrying out 30 cycles of PCR (30-sec denaturation at 95° C., 30-sec coupling at 55° C. and one-minute polymerization reaction at 72° C.) and then cooling down to 4° C. The carbonic anhydrase gene thus amplified was introduced into a pET-22b(+) vector using a NdeI/XhoI restriction enzyme to prepare a periplasmic expression vector for a carbonic anhydrase derived from *Neisseria gonorrhoeae*.

A carbonic anhydrase gene of *Synechocystis* was amplified using two primers of a *Synechocystis* genome DNA (i.e., forward primer: 5'-CCATGGGAGCCGAAGTTTCAT-TGATATCC-3' (SEQ ID NO: 22), and backward primer: 5'-CAAGCTTACGGGAGCCTCGATAAATGCGC-3' (SEQ ID NO: 18)), a Taq DNA polymerase, a dNTP mixed solution, and a PCR buffer by carrying out 30 cycles of PCR (30-sec denaturation at 95° C., 30-sec coupling at 55° C. and one-minute polymerization reaction at 72° C.) and then cooling down to 4° C. The carbonic anhydrase gene thus amplified was introduced into a GFT-removed pTTG vector (Korean Patent Application No. 2005-0099758, filed on Oct. 21, 2005) using a NcoI/HindIII restriction enzyme to prepare a periplasmic expression vector for a carbonic anhydrase derived from *Synechocystis*.

A carbonic anhydrase gene of *Escherichia coli* was amplified using two primers of a *Escherichia coli* genome DNA (i.e., forward primer: 5'-CCATGGGAAAAGATTAT-TGATGGATTC-3' (SEQ ID NO: 23), and backward primer: 5'-CAAGCTTCGCTGCGGTCGGTTGGCGTAG-3' (SEQ ID NO: 20)), a Taq DNA polymerase, a dNTP mixed solution, and a PCR buffer by carrying out 30 cycles of PCR (30-sec denaturation at 95° C., 30-sec coupling at 55° C. and one-minute polymerization reaction at 72° C.) and then cooling down to 4° C. The carbonic anhydrase gene thus amplified was introduced into a TorA-GFP-removed pTTG vector using a NcoI/HindIII restriction enzyme to prepare a periplasmic expression vector for a carbonic anhydrase derived from *Escherichia coli*.

1-3. Preparation of Vector for Cell Surface Expression

A carbonic anhydrase gene of *Neisseria gonorrhoeae* was amplified using two primers of a *Neisseria gonorrhoeae* genome DNA (i.e., forward primer: 5'-AGATCTCACG-GCAATCACACCCATTGG-3' (SEQ ID NO: 24), and backward primer: 5'-AAGCTTTCAGTGGTGGTGGTGGTG-GTG-3' (SEQ ID NO: 25)), a Taq DNA polymerase, a dNTP mixed solution, and a PCR buffer by carrying out 30 cycles of PCR (30-sec denaturation at 95° C., 30-sec coupling at 55° C. and one-minute polymerization reaction at 72° C.) and then cooling down to 4° C. The carbonic anhydrase gene thus amplified was introduced into a pINPNC-OPH vector (Li L, Kang D G, Cha H J. 2004, Biotechnol Bioeng 85:214-221) using a BglII/HindIII restriction enzyme to prepare a cell surface expression vector for a carbonic anhydrase derived from *Neisseria gonorrhoeae*.

Example 2

Preparation of Transformant Including Cytoplasmic, Periplasmic, or Cell Surface Expression Vector Each of the cytoplasmic expression vector, the periplasmic expression vector, and the cell surface expression vector produced in Examples 1-1, 1-2, and 1-3, respectively, was introduced into *Escherichia coli* BL21(DE3) by heat shock transformation at 42° C. for 2 minutes, to prepare a transformant including each vector and expressing a recombinant carbonic anhydrase. Each of the vector-inserted transformants was sorted out in an LB medium supplemented with ampicillin.

Example 3

Protein Expression and Preparation of Whole Cell Biocatalyst Using Each Transformant Each transformant prepared in Example 2 was cultured in a general LB medium (37° C.) supplemented with 50 μg/mL of ampicillin. When the absorbance ($OD_{600}$) of the culture sample reached 0.6 to 0.8, an expression-inducing factor, IPTG (isopropyl-D-thiogalactopyranoside), was added to induce protein expression. The cultured cell was then cultured at 25° C. for 20 more hours and then subjected to centrifugal separation at 4,000 rpm for 10 minutes. The culture sample was removed of the supernatant liquid to harvest cells, which were suspended in a solution for cell lysis (50 mM sodium phosphate buffer, 300 mM NaCl, pH 8) and destroyed with an ultrasonic pulverizer.

Example 3-1

Investigation of Cytoplasmic Expression

Figure 2:
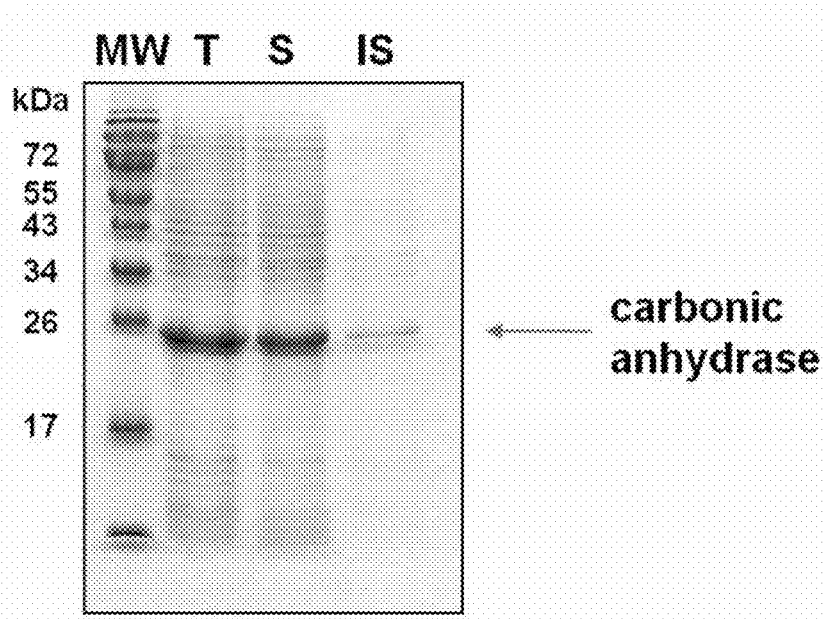
FIG. 2 presents the results of (A) SDS-PAGE analysis and (B) Western Blot analysis for a whole cell fraction (T), a soluble fraction (S), and an insoluble fraction (IS), when a carbonic anhydrase from *Neisseria gonorrhoeae* is expressed in cytoplasm.
Figure 2:
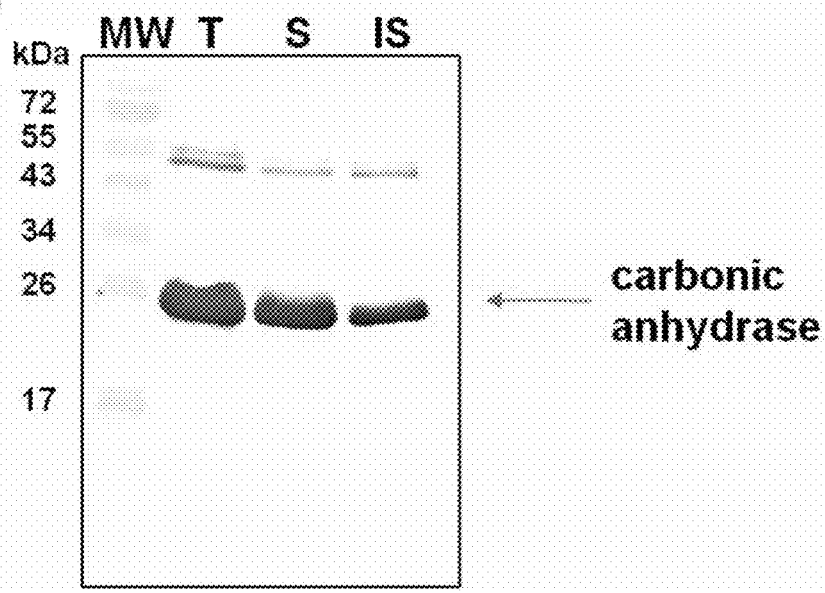

The destroyed cell including a cytoplasmic expression vector for a carbonic anhydrase from *Neisseria gonorrhoeae* was divided into a whole cell fraction (T) and its soluble fraction (S) and insoluble fraction (IS) and then subjected to SDS-PAGE and Western Blot analyses. As shown in FIG. 2, the analysis results revealed that the recombinant carbonic anhydrase was highly expressed in *Escherichia coli* with a molecular weight of about 25 kDa, which approximated the theoretical molecular weight of the carbonic anhydrase, 25.3 kDa. It was also revealed that the expressed protein was mostly folded into a native structure and expressed as the soluble fraction (lane S) having an activity.

Figure 3:
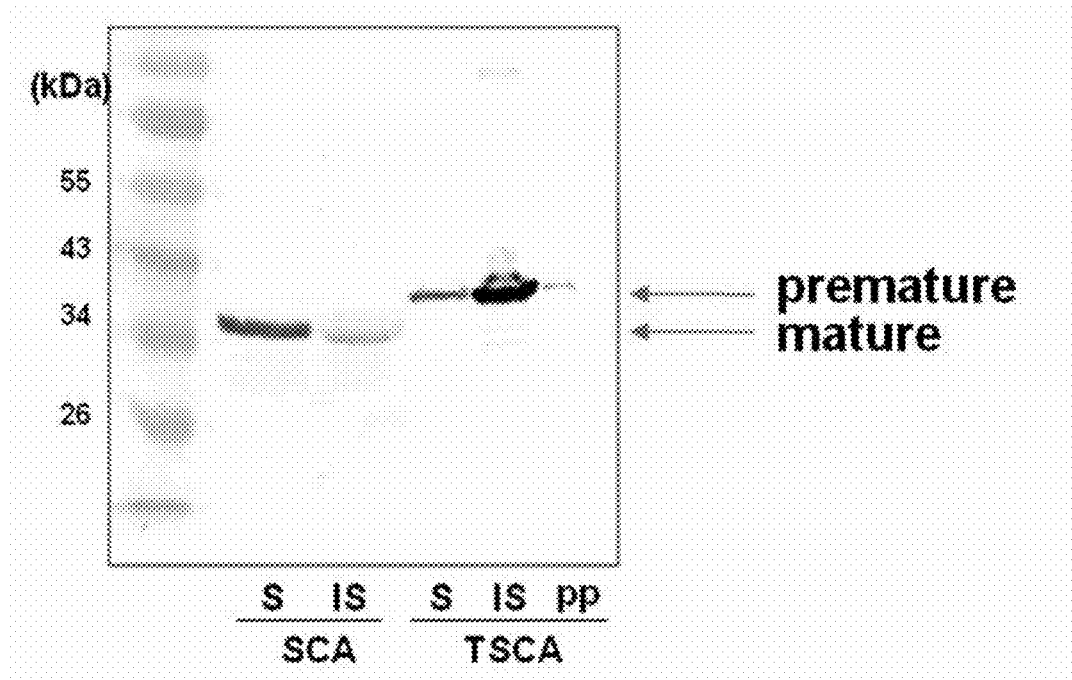
FIG. 3 presents the results of a Western Blot analysis for a soluble fraction (S), an insoluble fraction (IS), and a periplasmic fraction (PP), when a carbonic anhydrase from *Synechocystis* is expressed in cytoplasm (SCA) and periplasmic space (TSCA).

The destroyed cell (SCA) including a cytoplasmic expression vector of a carbonic anhydrase from *Synechocystis* was divided into a soluble fraction (S) and an insoluble fraction (IS) and then subjected to Western Blot analysis. As shown in FIG. 3, the recombinant carbonic anhydrase had a molecular weight of about 34 kDa approximating the theoretical molecular weight of the carbonic anhydrase. The protein was mostly expressed as the soluble fraction (lane S).

Figure 4:
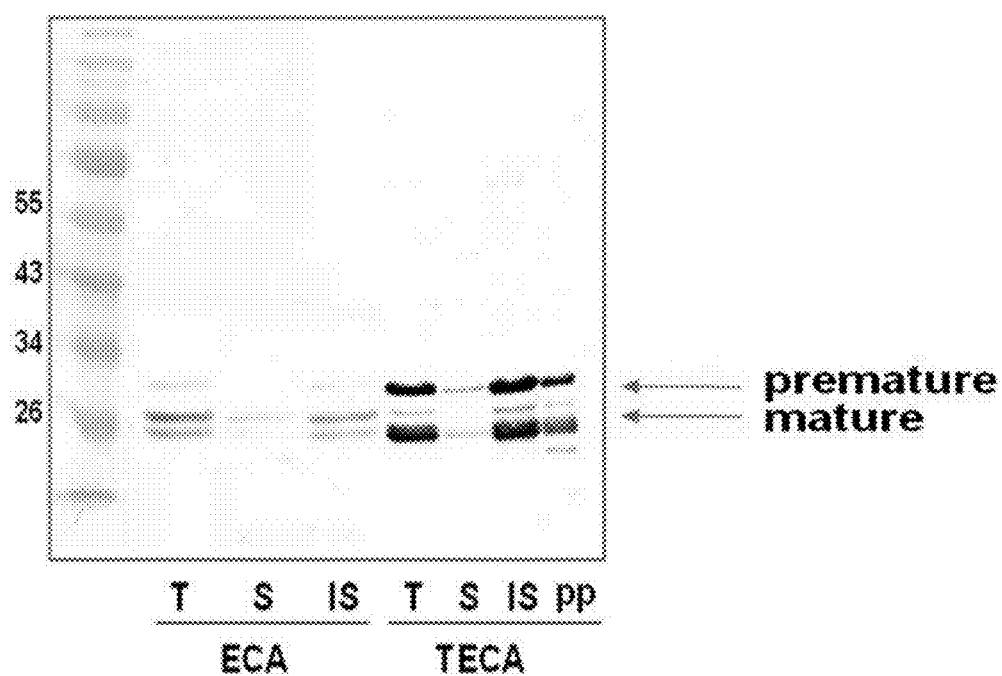
FIG. 4 presents the results of a Western Blot analysis for a whole cell fraction (T), a soluble fraction (S), an insoluble fraction (IS), and a periplasmic fraction (PP) when a carbonic anhydrase from *Escherichia coli* is expressed in cytoplasm (ECA) and periplasmic space (TECA).

The destroyed cell (ECA) including a cytoplasmic expression vector of a carbonic anhydrase from *Escherichia coli* was divided into a whole cell fraction (T), a soluble fraction (S), and an insoluble fraction (IS) and then subjected to Western Blot analysis. As shown in FIG. 4, the recombinant carbonic anhydrase had a molecular weight of about 23 kDa approximating the theoretical molecular weight of the carbonic anhydrase. But, the protein was mostly expressed as the insoluble fraction (lane IS).

Example 3-2

Investigation of Periplasmic Expression

The destroyed cell including a periplasmic expression vector for a carbonic anhydrase from *Neisseria gonorrhoeae* was divided into a whole cell fraction (T), a cell lysate (CL), a soluble fraction (S), an insoluble fraction (IS), and a periplasmic fraction (PP) and then subjected to Western Blot analysis. To obtain a periplasmic fraction, the cell lysate was centrifugally separately at 4,000 rpm for 10 minutes, removed of the supernatant liquid, suspended with a TEX buffer (50 mM tris, 3 mM EDTA, 0.1% Triton X-100, pH 8.0) and then stirred for one hour. Another centrifugal separation at 4,000 rpm for 10 more minutes turned the supernatant liquid into the periplasmic fraction (PP).

Figure 5:
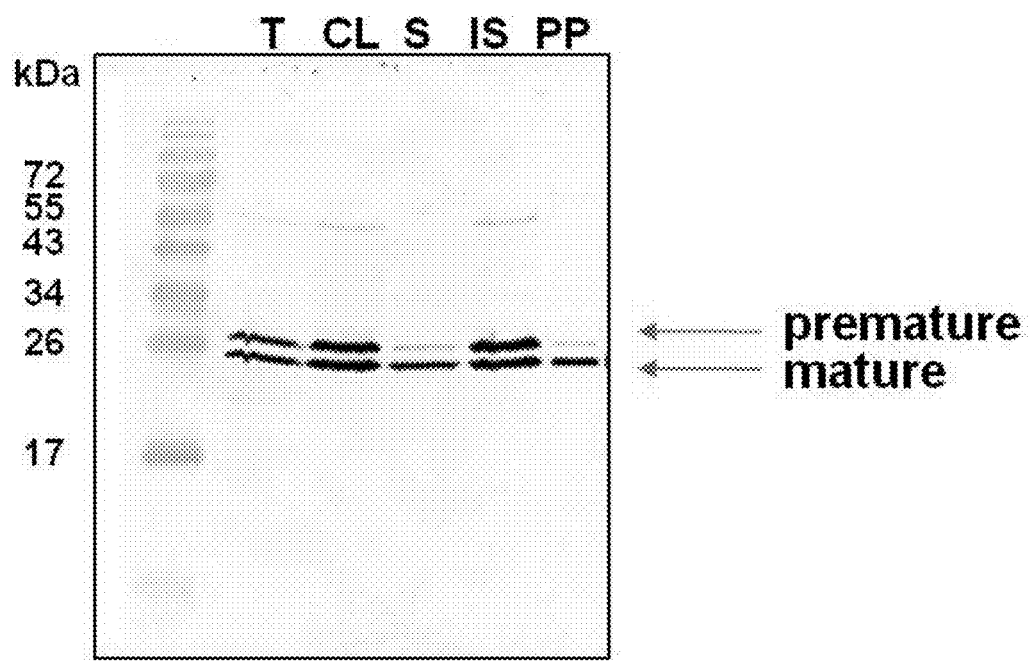
FIG. 5 presents the results of a Western Blot analysis for a whole cell fraction (T), a cell lysate (CL), a soluble fraction (S), an insoluble fraction (IS), and a periplasmic fraction (PP), when a carbonic anhydrase from *Neisseria gonorrhoeae* is expressed in periplasmic space.

As shown in FIG. 5, the recombinant carbonic anhydrase thus produced had a molecular weight which approximated both the theoretical molecular weights of a carbonic anhydrase expressed with a signal sequence (28 kDa) and a carbonic anhydrase expressed without a signal sequence (25.3 kDa). Further, a band detection in the periplasmic fraction showed that the recombinant carbonic anhydrase thus produced was successfully secreted into the periplasmic space (lane PP).

The destroyed cell (TSCA) including a periplasmic expression vector for a carbonic anhydrase from *Synechocystis* was divided into a soluble fraction (S), an insoluble fraction (IS), and a periplasmic fraction (PP) and then subjected to Western Blot analysis. As shown in FIG. 3, the recombinant carbonic anhydrase thus produced was not efficiently secreted into the periplasmic space.

The destroyed cell (TECA) including a periplasmic expression vector for a carbonic anhydrase from *Escherichia coli* was divided into a whole cell fraction (T), a soluble fraction (S), an insoluble fraction (IS), and a periplasmic fraction (PP) and then subjected to Western Blot analysis. As shown in FIG. 4, the recombinant carbonic anhydrase thus produced was secreted in large quantity into the periplasmic space (lane PP).

Example 3-3

Investigation of Cell Surface Expression

The destroyed cell including a cell surface expression vector for a carbonic anhydrase derived *Neisseria gonorrhoeae* was divided into a cell lysate (CL), a soluble fraction (S), an insoluble fraction (IS), and a cytoplasmic fraction (CP), and further into a cytoplasmic fraction and a cell membrane fraction in order to investigate the expression in a cell membrane fraction (TM). The process of preparing the cytoplasmic fraction and the cell membrane fraction was conducted as follows. The cultured cell was harvested after centrifugal separation, washed with PBS (130 mM NaCl, 2.5 mM KCl, 10 mM $Na_2HPO_4$, 1.7 mM $KH_2PO_4$) and then subjected to centrifugal separation at 9,000 rpm for 30 minutes.

With the supernatant liquid discarded, a solution containing 10 µg/ml of 1 mM EDTA in PBS was added to the cultured cell, which was stood for 2-hour reaction and then crushed with an ultrasonic pulverizer. The cell lysate thus obtained was centrifugally separated with an ultracentrifuge at 39,000 rpm for one hour to give a whole cell membrane fraction (TM) as the sediment and a cytoplasmic fraction (CP) as the supernatant.

Figure 6:
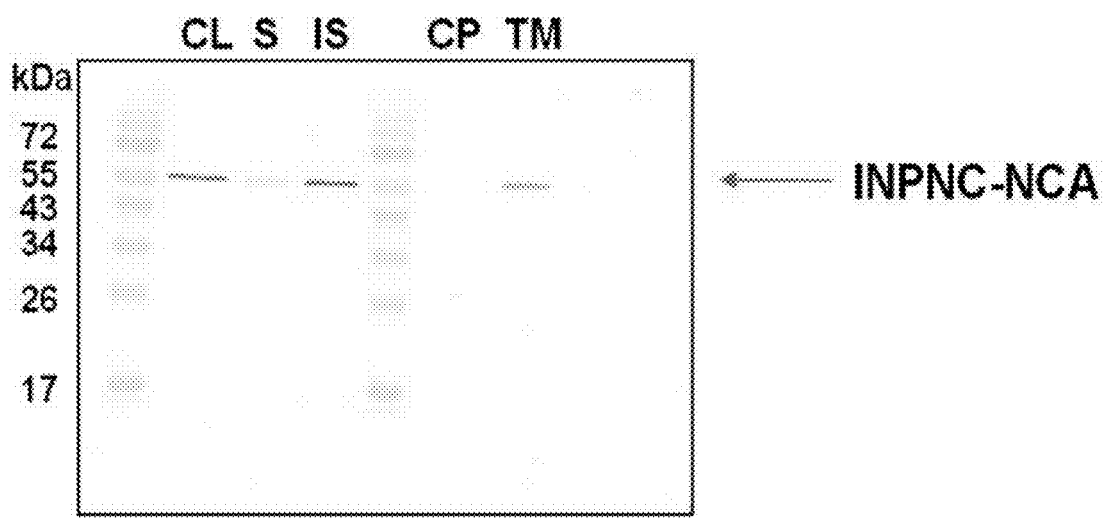
FIG. 6 presents the results of a Western Blot analysis for a cell lysate (CL), a soluble fraction (S), an insoluble fraction (IS), a cytoplasmic fraction (CP), and a cell membrane fraction (TM), when a carbonic anhydrase from *Neisseria gonorrhoeae* is expressed in cell surface.

As shown in FIG. 6, a protein band detected turned out to have a molecular weight of about 55 kDa, which was closely equivalent to the sum of the theoretical molecular weights of INPNC (25 kDa) and carbonic anhydrase (25.3 kDa) as expressed together, demonstrating the expression of the recombinant carbonic anhydrase in the cell surface (land TM). In fact, it has been reported that the protein expressed together with INPNC appeared to have a greater molecular weight than theoretically calculated (J. Biotechnol., vol. 118 (4), pp. 339-470).

Example 4

Purification of Carbonic Anhydrase Expressed in Cytoplasm

The soluble fraction of the whole cell biocatalyst from *Escherichia coli* that was prepared in Example 3-1 and proved out to express carbonic anhydrase in cytoplasm was subjected to nickel column chromatography to isolate and purify a protein. More specifically, a soluble fraction of protein was poured into a column filled with a nickel resin, so the column absorbed the protein. Then a wash buffer (50 mM sodium phosphate buffer, 300 mM NaCl, 40 mM imidazole, pH 8.0) was used to wash away the protein not bound to the column. The protein was eluted from the column with a 50 mM sodium phosphate buffer, 300 mM NaCl, and 250 mM imidazole (pH 8.0). The purified solution was then dialyzed using 100 mM tris-sulfate (pH 7.6) to eliminate the salts.

Figure 7:
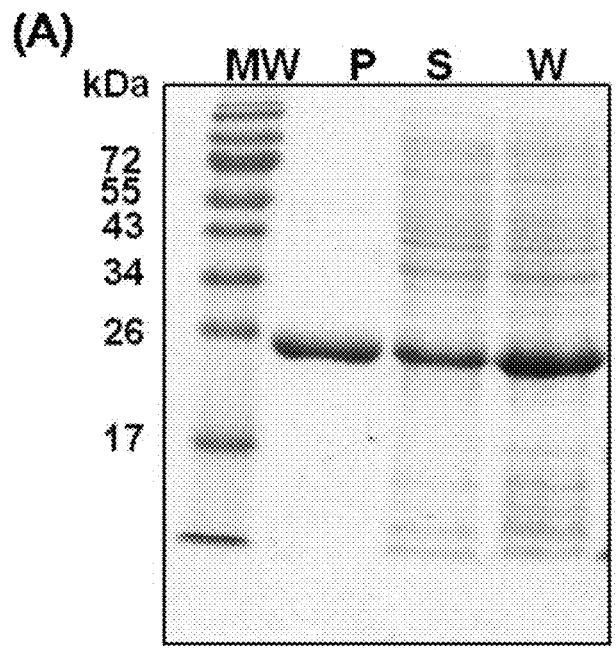
FIG. 7 presents the results of (A) SDS-PAGE analysis and (B) Western Blot analysis for a whole cell (W), a soluble fraction (S) and a purified fraction (P) of a transformant, where a carbonic anhydrase from *Neisseria gonorrhoeae* is expressed in cytoplasm.
Figure 7:
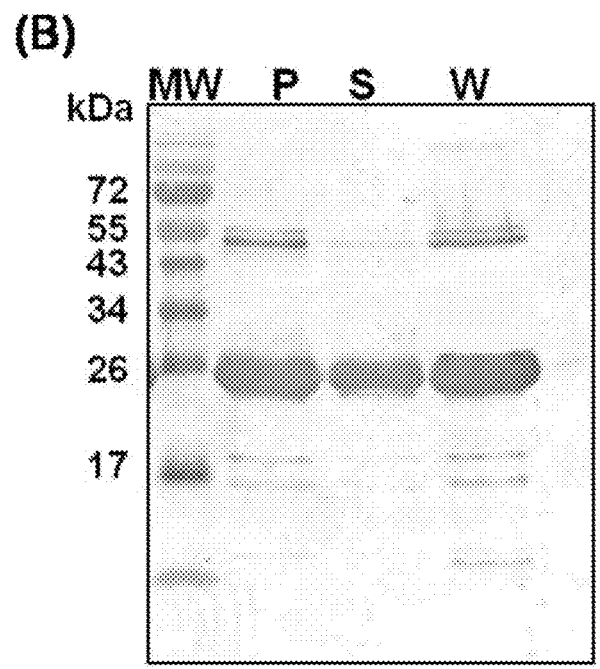

FIG. 7 shows the results of (A) SDS-PAGE analysis and (B) Western Blot analysis for the purified protein (P), the whole cell fraction (W), and the soluble fraction (S). As can be seen from FIG. 7, the isolation and purification yielded the recombinant carbonic anhydrase with a high purity of 99% or greater (land P). Further, the produced amount of the carbonic anhydrase protein was 10.6.2 mg/L, which was about 70% of the total amount of the protein (1.51.7 mg/L), and the carbonic anhydrase protein was purified to give 66.7 mg/l of pure carbonic anhydrase with the purification yield of 62.8%.

Example 5

Measurement of Activity on Hydration of Carbon Dioxide Using Isolated/Purified Carbonic Anhydrase and Recombinant Whole Cell Biocatalyst The activity on the hydration of carbon dioxide was measured in the case of using the protein (NCA) purified in Example 4, or the soluble fraction (S) and the whole cell (W) of the *Escherichia coli* whole cell biocatalyst of Example 3 where a carbonic anhydrase was expressed in cytoplasm. The positive control was commercial bovine carbonic anhydrase (BCA) extracted from bovine serum, and the negative control was bovine serum albumin (BSA) inactive on the hydration of carbon dioxide. For the measurement of activity, each fraction with a 20 mM tris-sulfate buffer (pH 8.3) and a $CO_2$-saturated $H_2O$ solution was investigated in regard to the required time to reduce the pH value from 8.0 to 7.0. The faster drop of the pH value indicates the higher $CO_2$ capturing activity.

Figure 8:
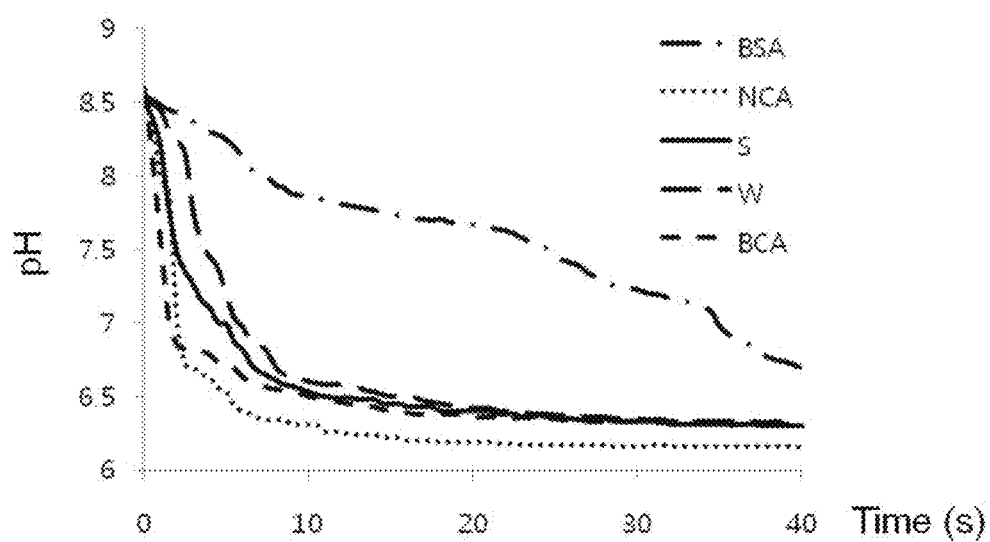
FIG. 8 presents the measurement results of the catalytic activity on hydration of carbon dioxide for a whole cell (W), a soluble fraction (S) and a purified fraction (NCA) of a transformant in which a carbonic anhydrase from *Neisseria gonorrhoeae* is expressed in cytoplasm. Here, BSA is bovine serum albumin as a negative control, and BCA is bovine carbonic anhydrase as a positive control.

As shown in FIG. 8, the purified carbonic anhydrase (NCA; ~2,200 U/mg) had the $CO_2$ capturing activity that was about 71% of the activity of the BCA (3,090 U/mg). Further, the non-purified fractions, that is, the solution fraction (S; ~920 U/mg) and the whole cell (W; ~730 U/mg) also had a high activity on the hydration of carbon dioxide.

Example 6

Precipitation of Calcium Carbonate Using Calcium Ion

Using a 200 mM tris-sulfate buffer (pH 10.5) and a 100 mM $CaCl_2$ solution as a source of calcium ions, the precipitation of calcium carbonate was induced in the negative control (BSA) and the positive control (BCA) of Example 5, three samples of cytoplasmic expression cells (i.e., purified carbonic anhydrase, solution fraction, and whole cell), and the periplasmic expression whole cell. More specifically, the buffer and the $CaCl_2$ solution (each 20 mL) were mixed with each sample. Under agitation, $CO_2$ gas was injected into the mixture at a defined flow rate to investigate the precipitation behavior.

Figure 9:
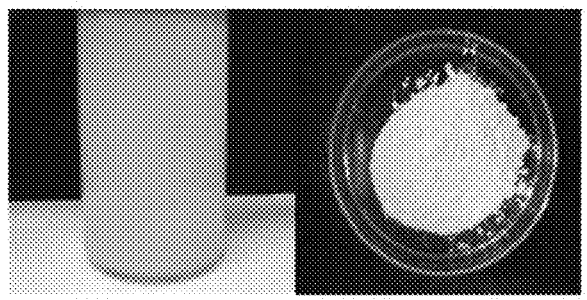
FIG. 9 presents pictures showing the precipitate shape and dried calcium carbonate powder two minutes after the initial reaction for forming a calcium carbonate precipitate using a whole cell, a soluble fraction and a purified fraction of a transformant in which a carbonic anhydrase from *Neisseria gonorrhoeae* is expressed in cytoplasm, a positive control (BSA), and a negative control (BCA).
Figure 9:
Figure 9:
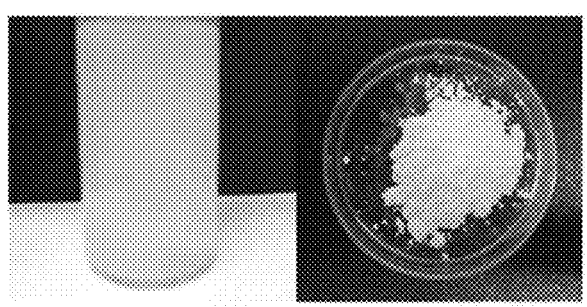
Figure 9:
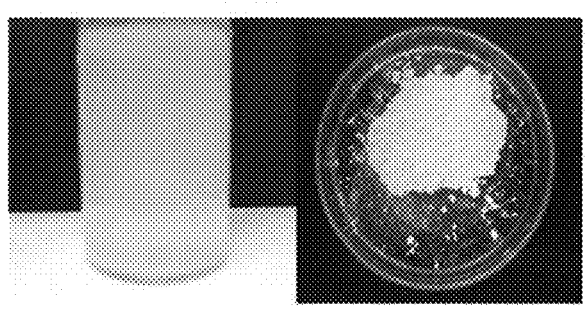
Figure 9:
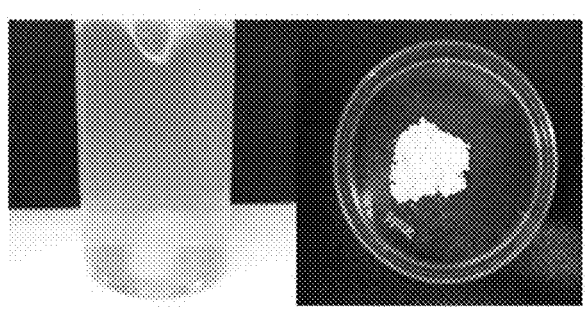

FIG. 9 shows a quantitative comparison of precipitate powders prepared by filtering the precipitates produced 2 minutes after the supply of $CO_2$ gas through a 0.2 μm membrane filter and drying at 80° C. for about 30 minutes. Due to the function of the carbonic anhydrase, the precipitation as well as the catalyzation on hydration of carbon dioxide was accelerated in the BCA, the purified fraction, the solution fraction, and the cytoplasmic expression whole cell other than the BSA. The precipitate obtained from each sample was dried to yield calcium carbonate powder in large quantity.

Using a 200 mM tris-Cl buffer (pH 10.8) and a 500 mM $CaCl_2$ solution as a source of calcium ions, the precipitation of calcium carbonate was induced in the three samples of whole cells (i.e., the negative control, the cytoplasmic expression whole cell, and the periplasmic expression whole cell). The negative control whole cell was *Escherichia coli* cells containing a pET22(+) vector alone. More specifically, the buffer (23 mL) and the $CaCl_2$ solution (6 mL) were mixed with each whole cell. Under agitation, $CO_2$ gas was injected into the mixture at a defined flow rate to investigate the precipitation behavior.

Figure 10:
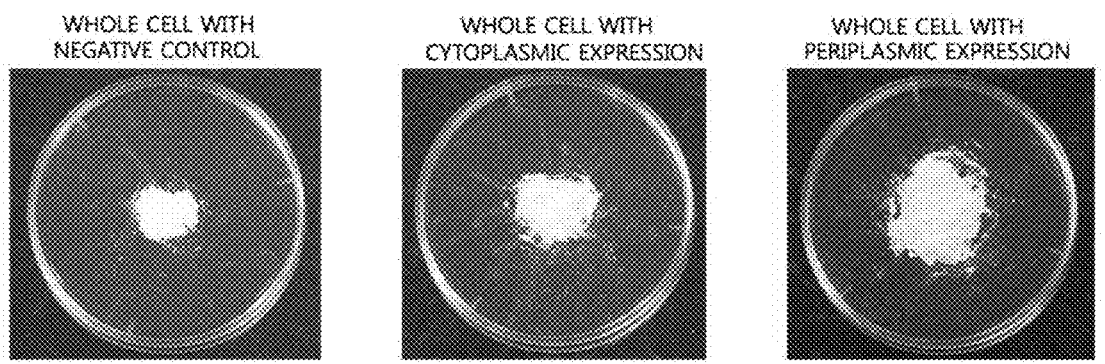
FIG. 10 presents pictures showing the dried calcium carbonate powder one minute after the initial reaction for forming a calcium carbonate precipitate using a whole cell in which a carbonic anhydrase from *Neisseria gonorrhoeae* is expressed in cytoplasm or periplasmic space.

FIG. 10 shows a quantitative comparison of precipitate powders prepared by filtering the precipitates produced one minute after the supply of $CO_2$ gas through a 0.2 μm membrane filter and drying at 80° C. for about 30 minutes. As a result, the periplasmic expression whole cell yielded calcium carbonate powder about 6.3 times as much as the negative control and about 2.6 times as much as the cytoplasmic expression whole cell. Accordingly, the periplasmic expression, which reduces inhibition of material transfer by the cell membranes, can be an effective means for using the whole cell as a biocatalyst.

Example 7

Identification of Calcium Carbonate

Figure 11:
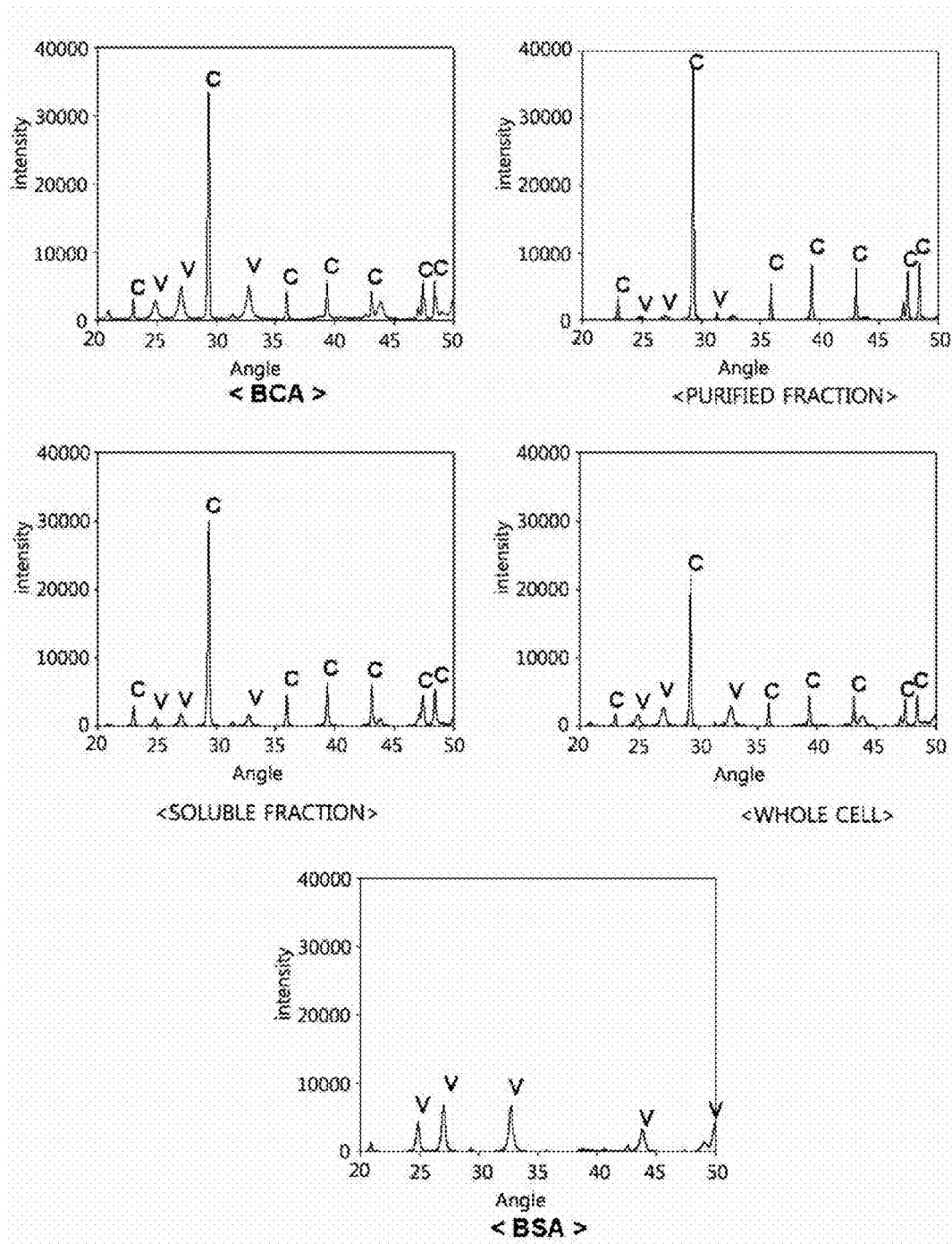
FIG. 11 shows the results of X-ray diffraction on each calcium carbonate powder of FIG. 9 to identify the crystal type.
Figure 12:
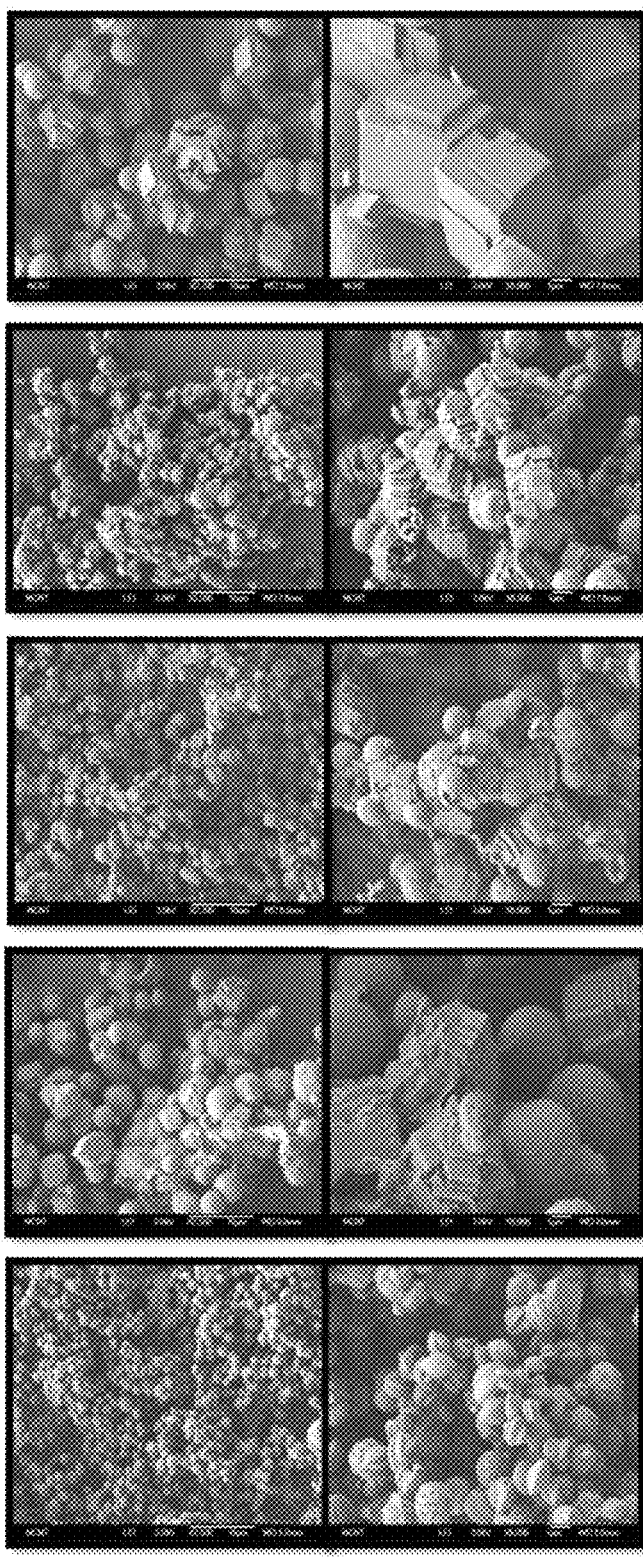
FIG. 12 shows scanning electron microscope (SEM) pictures of each calcium carbonate powder of FIG. 9 to identify the crystal shape.
Figure 13:
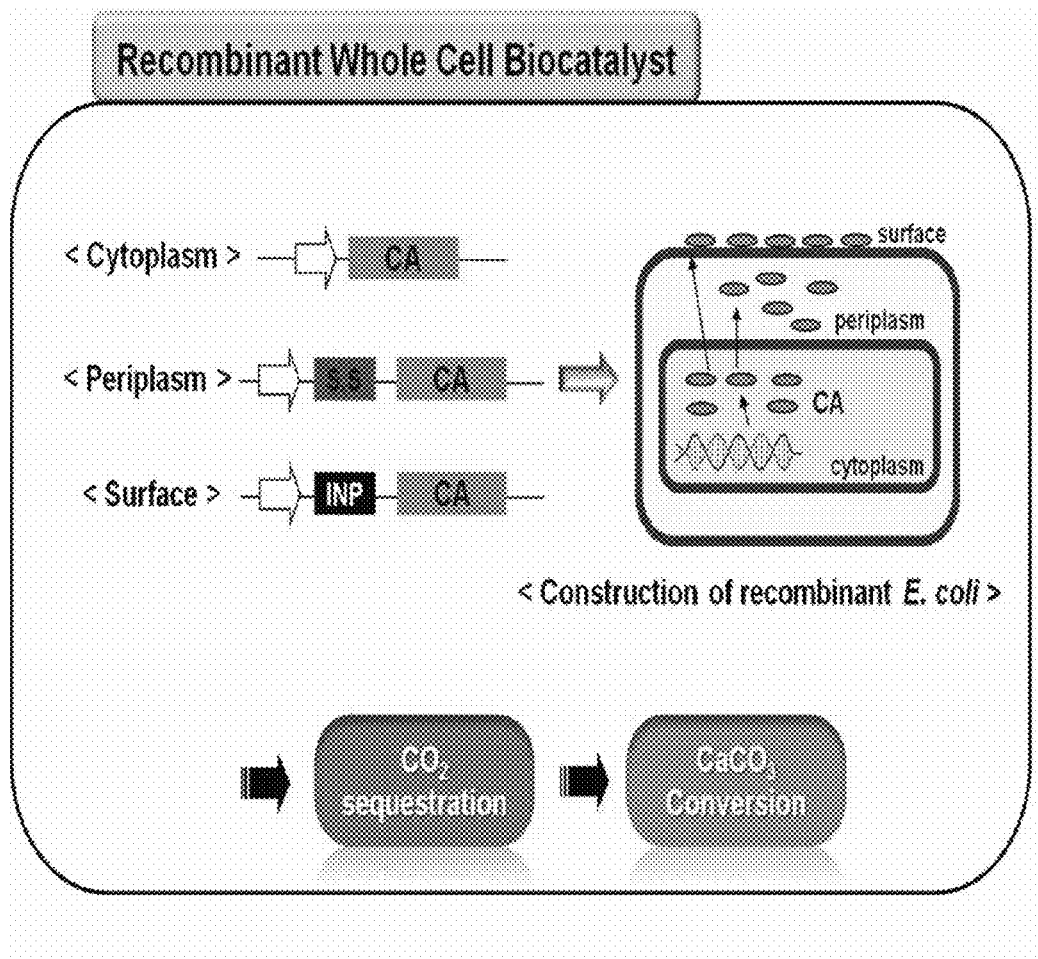
FIG. 13 is a mimetic diagram showing the process of capturing carbon dioxide and converting it to a carbonate using a recombinant whole cell biocatalyst expressing a recombinant carbonic anhydrase in cytoplasm, periplasmic space, or cell surface of a transformant cell.

Each powder obtained in Example 6 was identified as calcium carbonate crystals according to X-ray diffraction and SEM analyses. According to the X-ray diffraction peak patterns as shown in FIG. 11, the precipitate was calcium carbonate crystals consisting of calcite and vaterite together. The carbonic anhydrase of the positive control (BCA), the purified carbonic anhydrase, the soluble fraction, and the whole cell accelerated the transition of vaterite into calcite as well as precipitation. The negative control (BSA) having no enzymatic activity appeared to have little transition of vaterite into calcite due to retarded precipitation. As shown in FIG. 12, the precipitate was identified as calcium carbonate crystals with co-existence of parallelepiped calcite and spherical vaterite according to SEM analysis. Also, the use of the carbonic anhydrase accelerated the transition of vaterite into calcite as well as precipitation.

The invention claimed is:

1. A composition for capturing carbon dioxide, the composition comprising at least one selected from the group consisting of:
   an isolated host cell transformed with a vector comprising a heterologous nucleic acid encoding a recombinant carbonic anhydrase;
   a cell lysate of the isolated host cell, or a fraction thereof; and
   a carbonic anhydrase isolated from the isolated host cell, wherein the carbonic anhydrase has the amino acid sequence of SEQ ID NO: 3.

2. The composition as claimed in claim 1, wherein the isolated host cell has an expression of carbonic anhydrase in periplasmic space.

3. The composition as claimed in claim 1, wherein the fraction of the cell lysate includes an isolated host cell fraction, a soluble fraction, an insoluble fraction, or a periplasmic fraction of the cell lysate.

4. The composition as claimed in claim 1, wherein the carbonic anhydrase is obtained from *Neisseria gonorrhoea*.

5. The composition as claimed in claim 1, wherein the nucleic acid encoding the carbonic anhydrase has the nucleic acid sequence of SEQ ID NO: 4.

6. The composition as claimed in claim 1, wherein the isolated host cell is *Escherichia coli*.

7. A composition for converting carbon dioxide to a carbonate or a bicarbonate, the composition comprising:
   the composition as claimed in claim 1; and
   a metal cation.

8. The composition as claimed in claim 7, wherein the metal cation is Na+, Ca2+, Fe2+, Mn2+, Sr2+, Ca2+, Ba2+, Zn2+, or Pb2+; or a nitrate, hydrochloride, hydrate or solution thereof.

9. The composition as claimed in claim 7, wherein the carbonate is sodium carbonate, calcium carbonate, iron carbonate, manganese carbonate, strontium carbonate, barium carbonate, zinc carbonate, or lead carbonate.

10. A method for capturing carbon dioxide comprising:
    preparing the carbon dioxide capturing composition as claimed in claim 1; and
    feeding carbon dioxide into the carbon dioxide capturing composition.

11. A method for converting carbon dioxide to a carbonate or a bicarbonate comprising:
    (a) preparing the carbon dioxide capturing composition as claimed in claim 1; and
    (b) feeding a metal cation and carbon dioxide into the carbon dioxide capturing composition.

12. The method as claimed in claim 11, wherein the step (b) of feeing a metal cation and carbon dioxide into the carbon dioxide capturing composition comprises:
    feeding a metal cation and carbon dioxide in sequence,
    feeding carbon dioxide and a metal cation in sequence, or
    feeding a metal cation and carbon dioxide at once.

13. The method as claimed in claim 11, wherein the metal cation is $Na^+$, $Ca^{2+}$, $Fe^{2+}$, $Mn^{2+}$, $Sr^{2+}$, $Ca^{2+}$, $Ba^{2+}$, $Zn^{2+}$, or $Pb^{2+}$; or a nitrate, hydrochloride, hydrate or solution thereof.

14. The method as claimed in claim 11, wherein the carbonate is sodium carbonate, calcium carbonate, iron carbonate, manganese carbonate, strontium carbonate, barium carbonate, zinc carbonate, or lead carbonate.

* * * * *

SEQUENCE LISTING

```
<160> NUMBER OF SEQ ID NOS: 25

<210> SEQ ID NO 1
<211> LENGTH: 240
<212> TYPE: PRT
<213> ORGANISM: Neisseria gonorrhoeae
<220> FEATURE:
<221> NAME/KEY: PEPTIDE
<222> LOCATION: (1)..(240)
<223> OTHER INFORMATION: carbonic anhydrase (cytoplasmic expression)

<400> SEQUENCE: 1

Met His Gly Asn His Thr His Trp Gly Tyr Thr Gly His Asp Ser Pro
  1               5                  10                  15

Glu Ser Trp Gly Asn Leu Ser Glu Glu Phe Arg Leu Cys Ser Thr Gly
             20                  25                  30

Lys Asn Gln Ser Pro Val Asn Ile Thr Glu Thr Val Ser Gly Lys Leu
         35                  40                  45

Pro Ala Ile Lys Val Asn Tyr Lys Pro Ser Met Val Asp Val Glu Asn
     50                  55                  60

Asn Gly His Thr Ile Gln Val Asn Tyr Pro Glu Gly Gly Asn Thr Leu
 65                  70                  75                  80

Thr Val Asn Gly Arg Thr Tyr Thr Leu Lys Gln Phe His Phe His Val
                 85                  90                  95

Pro Ser Glu Asn Gln Ile Lys Gly Arg Thr Phe Pro Met Glu Ala His
            100                 105                 110

Phe Val His Leu Asp Glu Asn Lys Gln Pro Leu Val Leu Ala Val Leu
        115                 120                 125
```

```
Tyr Glu Ala Gly Lys Thr Asn Gly Arg Leu Ser Ser Ile Trp Asn Val
            130                 135                 140

Met Pro Met Thr Ala Gly Lys Val Lys Leu Asn Gln Pro Phe Asp Ala
145                 150                 155                 160

Ser Thr Leu Leu Pro Lys Arg Leu Lys Tyr Tyr Arg Phe Ala Gly Ser
                165                 170                 175

Leu Thr Thr Pro Pro Cys Thr Glu Gly Val Ser Trp Leu Val Leu Lys
            180                 185                 190

Thr Tyr Asp His Ile Asp Gln Ala Gln Ala Glu Lys Phe Thr Arg Ala
                195                 200                 205

Val Gly Ser Glu Asn Asn Arg Pro Val Gln Pro Leu Asn Ala Arg Val
210                 215                 220

Val Ile Glu Lys Leu Ala Ala Ala Leu Glu His His His His His His
225                 230                 235                 240

<210> SEQ ID NO 2
<211> LENGTH: 723
<212> TYPE: DNA
<213> ORGANISM: Neisseria gonorrhoeae
<220> FEATURE:
<221> NAME/KEY: gene
<222> LOCATION: (1)..(723)
<223> OTHER INFORMATION: carbonic anhydrase (cytoplasmic expression)

<400> SEQUENCE: 2
atgcacggca atcacaccca ttggggctat accggacacg actctcccga aagctggggc        60
aatctgtcag aagaattccg tttgtgctcc accggcaaaa accaatctcc ggtaaacatt       120
accgaaaccg tttccggcaa actgcccgcc atcaaagtca attacaaacc gagtatggtt       180
gacgtggaaa caacggcca caccattcag gtcaattatc ccgaaggcgg caataccctg       240
accgtgaacg gccgcaccta taccctgaaa cagttccact tccacgtgcc gagcgaaaac       300
caaatcaaag gccgcacttt cccgatggaa gctcacttcg tccacttaga cgaaaacaaa       360
cagcctttag tattagccgt gctgtatgaa gccggcaaaa ccaacggccg cctgtcttcc       420
atctggaacg tcatgccgat gaccgcagga aaagtgaaac tcaaccaacc gttcgacgca       480
tccaccctac tgccgaaacg gttgaaatac taccgctttg ccggttcgct gaccacgccg       540
ccgtgcacag agggcgtatc atggttggtg ttgaaaactt atgaccacat cgaccaagcg       600
caagcggaaa aattcacccg cgccgtcggt tcggaaaaca accgcccgt acagcctctg       660 aatgcacgtg tagttattga aaagcttgcg ccgcactcg agcaccacca ccaccaccac       720
tga                                                                    723

<210> SEQ ID NO 3
<211> LENGTH: 284
<212> TYPE: PRT
<213> ORGANISM: Neisseria gonorrhoeae
<220> FEATURE:
<221> NAME/KEY: PEPTIDE
<222> LOCATION: (1)..(284)
<223> OTHER INFORMATION: carbonic anhydrase (periplasmic expression)

<400> SEQUENCE: 3

Met Asn Asn Asn Asp Leu Phe Gln Ala Ser Arg Arg Arg Phe Leu Ala
 1               5                  10                  15

Gln Leu Gly Gly Leu Thr Val Ala Gly Met Leu Gly Pro Ser Leu Leu
                20                  25                  30

Thr Pro Arg Arg Ala Thr Ala Ala Gln Ala Ala Met Gly His Gly Asn
            35                  40                  45
```

```
His Thr His Trp Gly Tyr Thr Gly His Asp Ser Pro Glu Ser Trp Gly
         50                  55                  60
Asn Leu Ser Glu Glu Phe Arg Leu Cys Ser Thr Gly Lys Asn Gln Ser
 65                  70                  75                  80
Pro Val Asn Ile Thr Glu Thr Val Ser Gly Lys Leu Pro Ala Ile Lys
                 85                  90                  95
Val Asn Tyr Lys Pro Ser Met Val Asp Val Glu Asn Asn Gly His Thr
            100                 105                 110
Ile Gln Val Asn Tyr Pro Glu Gly Gly Asn Thr Leu Thr Val Asn Gly
        115                 120                 125
Arg Thr Tyr Thr Leu Lys Gln Phe His Phe His Val Pro Ser Glu Asn
    130                 135                 140
Gln Ile Lys Gly Arg Thr Phe Pro Met Glu Ala His Phe Val His Leu
145                 150                 155                 160
Asp Glu Asn Lys Gln Pro Leu Val Leu Ala Val Leu Tyr Glu Ala Gly
                165                 170                 175
Lys Thr Asn Gly Arg Leu Ser Ser Ile Trp Asn Val Met Pro Met Thr
            180                 185                 190
Ala Gly Lys Val Lys Leu Asn Gln Pro Phe Asp Ala Ser Thr Leu Leu
        195                 200                 205
Pro Lys Arg Leu Lys Tyr Tyr Arg Phe Ala Gly Ser Leu Thr Thr Pro
    210                 215                 220
Pro Cys Thr Glu Gly Val Ser Trp Leu Val Leu Lys Thr Tyr Asp His
225                 230                 235                 240
Ile Asp Gln Ala Gln Ala Glu Lys Phe Thr Arg Ala Val Gly Ser Glu
                245                 250                 255
Asn Asn Arg Pro Val Gln Pro Leu Asn Ala Arg Val Val Ile Glu Lys
            260                 265                 270
Leu Ala Ala Ala Leu Glu His His His His His His
        275                 280

<210> SEQ ID NO 4
<211> LENGTH: 855
<212> TYPE: DNA
<213> ORGANISM: Neisseria gonorrhoeae
<220> FEATURE:
<221> NAME/KEY: gene
<222> LOCATION: (1)..(855)
<223> OTHER INFORMATION: carbonic anhydrase (periplasmic expression)

<400> SEQUENCE: 4
atgaacaata acgatctctt tcaggcatca cgtcggcgtt ttctggcaca actcggcggc      60
ttaaccgtcg ccgggatgct ggggccgtca ttgttaacgc cgcgacgtgc gactgcggcg     120
caagcggcca tgggacacgg caatcacacc cattggggct ataccggaca cgactctccc     180
gaaagctggg gcaatctgtc agaagaattc cgtttgtgct ccaccggcaa aaaccaatct     240
ccggtaaaca ttaccgaaac cgtttccggc aaactgcccg ccatcaaagt caattacaaa     300
ccgagtatgg ttgacgtgga aaacaacggc cacaccattc aggtcaatta tcccgaaggc     360
ggcaataccc tgaccgtgaa cggccgcacc tatacccctga aacagttcca cttccacgtg     420
ccgagcgaaa accaaatcaa aggccgcact ttcccgatgg aagctcactt cgtccactta     480
gacgaaaaca aacagccttt agtattagcc gtgctgtatg aagccggcaa aaccaacggc     540
cgcctgtctt ccatctggaa cgtcatgccg atgaccgcag gaaaagtgaa actcaaccaa     600
ccgttcgacg catccaccct actgccgaaa cggttgaaat actaccgctt tgccggttcg     660
```

-continued

```
ctgaccacgc cgccgtgcac agagggcgta tcatggttgg tgttgaaaac ttatgaccac    720
atcgaccaag cgcaagcgga aaaattcacc cgcgccgtcg gttcggaaaa caaccgcccc    780
gtacagcctc tgaatgcacg tgtagttatt gaaaagcttg cggccgcact cgagcaccac    840
caccaccacc actga                                                    855
```

```
<210> SEQ ID NO 5
<211> LENGTH: 462
<212> TYPE: PRT
<213> ORGANISM: Neisseria gonorrhoeae
<220> FEATURE:
<221> NAME/KEY: PEPTIDE
<222> LOCATION: (1)..(462)
<223> OTHER INFORMATION: carbonic anhydrase (cell surface expression)

<400> SEQUENCE: 5

Met Ala Leu Asp Lys Ala Leu Val Leu Arg Thr Cys Ala Asn Asn Met
  1               5                  10                  15

Ala Asp His Cys Gly Leu Ile Trp Pro Ala Ser Gly Thr Val Glu Ser
                 20                  25                  30

Arg Tyr Trp Gln Ser Thr Arg Arg His Glu Asn Gly Leu Val Gly Leu
             35                  40                  45

Leu Trp Gly Ala Gly Thr Ser Ala Phe Leu Ser Val His Ala Asp Ala
         50                  55                  60

Arg Trp Ile Val Cys Glu Val Ala Val Ala Asp Ile Ile Ser Leu Glu
 65                  70                  75                  80

Glu Pro Gly Met Val Lys Phe Pro Arg Ala Glu Val Val His Val Gly
                 85                  90                  95

Asp Arg Ile Ser Ala Ser His Phe Ile Ser Ala Arg Gln Ala Asp Pro
            100                 105                 110

Ala Ser Thr Ser Thr Ser Thr Ser Thr Leu Thr Pro Met Pro
        115                 120                 125

Thr Ala Ile Pro Thr Pro Met Pro Ala Val Ala Ser Val Thr Leu Pro
    130                 135                 140

Val Ala Glu Gln Ala Arg His Glu Val Phe Asp Val Ala Ser Val Ser
145                 150                 155                 160

Ala Ala Ala Ala Pro Val Asn Thr Leu Pro Val Thr Thr Pro Gln Asn
                165                 170                 175

Leu Gln Thr Arg Ser Arg Leu Trp Asp Gly Lys Arg Tyr Arg Gln Leu
            180                 185                 190

Val Ala Arg Thr Gly Glu Asn Gly Val Glu Ala Asp Ile Pro Tyr Tyr
        195                 200                 205

Val Asn Glu Asp Asp Ile Val Asp Lys Pro Asp Glu Asp Asp
    210                 215                 220

Trp Ile Glu Val His Gly Asn His Thr His Trp Gly Tyr Thr Gly His
225                 230                 235                 240

Asp Ser Pro Glu Ser Trp Gly Asn Leu Ser Glu Phe Arg Leu Cys
                245                 250                 255

Ser Thr Gly Lys Asn Gln Ser Pro Val Asn Ile Thr Glu Thr Val Ser
            260                 265                 270

Gly Lys Leu Pro Ala Ile Lys Val Asn Tyr Lys Pro Ser Met Val Asp
        275                 280                 285

Val Glu Asn Asn Gly His Thr Ile Gln Val Asn Tyr Pro Glu Gly Gly
    290                 295                 300
```

Asn Thr Leu Thr Val Asn Gly Arg Thr Tyr Thr Leu Lys Gln Phe His
305                 310                 315                 320

Phe His Val Pro Ser Glu Asn Gln Ile Lys Gly Arg Thr Phe Pro Met
            325                 330                 335

Glu Ala His Phe Val His Leu Asp Glu Asn Lys Gln Pro Leu Val Leu
        340                 345                 350

Ala Val Leu Tyr Glu Ala Gly Lys Thr Asn Gly Arg Leu Ser Ser Ile
    355                 360                 365

Trp Asn Val Met Pro Met Thr Ala Gly Lys Val Lys Leu Asn Gln Pro
    370                 375                 380

Phe Asp Ala Ser Thr Leu Leu Pro Lys Arg Leu Lys Tyr Tyr Arg Phe
385                 390                 395                 400

Ala Gly Ser Leu Thr Thr Pro Pro Cys Thr Glu Gly Val Ser Trp Leu
            405                 410                 415

Val Leu Lys Thr Tyr Asp His Ile Asp Gln Ala Gln Ala Glu Lys Phe
            420                 425                 430

Thr Arg Ala Val Gly Ser Glu Asn Asn Arg Pro Val Gln Pro Leu Asn
        435                 440                 445

Ala Arg Val Val Ile Glu Leu Glu His His His His His
450                 455                 460

<210> SEQ ID NO 6
<211> LENGTH: 1389
<212> TYPE: DNA
<213> ORGANISM: Neisseria gonorrhoeae
<220> FEATURE:
<221> NAME/KEY: gene
<222> LOCATION: (1)..(1389)
<223> OTHER INFORMATION: carbonic anhydrase (cell surface expression)

<400> SEQUENCE: 6

```
atggctctcg acaaggcgtt ggtgctgcgt acctgtgcaa ataacatggc cgatcactgc      60
ggccttatat ggcccgcgtc cggcacggtg gaatccagat actggcagtc aaccaggcgg     120
catgagaatg gtctggtcgg tttactgtgg ggcgctggaa ccagcgcttt tctaagcgtg     180
catgccgatg ctcgatggat tgtctgtgaa gttgccgttg cagacatcat cagtctggaa     240
gagccgggaa tggtcaagtt ccgcggggcc gaggtggttc atgtcggcga caggatcagc     300
gcgtcacact tcatttcggc acgtcaggcc gaccctgcgt caacgtcaac gtcaacgtca     360
acgtcaacgt taacgccaat gcctacggcc atacccacgc ccatgcctgc ggtagcaagt     420
gtcacgttac cggtggccga acaggcccgt catgaagtgt tcgatgtcgc gtcggtcagc     480
gcggctgccg ccccagtaaa caccctgccg gtgacgacgc cgcagaattt gcagaccaga     540
tcaagactct gggacgggaa gaggtacagg caactggtcg ccagaacggg tgagaacggt     600
gttgaggccg acataccgta ttacgtgaac gaagatgacg atattgtcga taaacccgac     660
gaggacgatg actggataga ggtacacggc aatcacaccc attggggcta taccggacac     720
gactctcccg aaagctgggg caatctgtca gaagaattcc gtttgtgctc caccggcaaa     780
aaccaatctc cggtaaacat taccgaaacc gtttccggca aactgcccgc catcaaagtc     840
aattacaaac cgagtatggt tgacgtgaaa acaacggcc acaccattca ggtcaattat     900
cccgaaggcg gcaatacccc tgaccgtgaa cggccgcacct atccctgaa acagttccac     960
ttccacgtgc cgagcgaaaa ccaaatcaaa ggccgcactt tcccgatgga agctcacttc    1020
gtccacttag acgaaaacaa acagcccttta gtattagccg tgctgtatga agccggcaaa    1080
accaacggcc gcctgtcttc catctggaac gtcatgccga tgaccgcagg aaaagtgaaa    1140
```

```
ctcaaccaac cgttcgacgc atccacccta ctgccgaaac ggttgaaata ctaccgcttt   1200
gccggttcgc tgaccacgcc gccgtgcaca gagggcgtat catggttggt gttgaaaact   1260
tatgaccaca tcgaccaagc gcaagcggaa aaattcaccc gcgccgtcgg ttcggaaaac   1320
aaccgccccg tacagcctct gaatgcacgt gtagttattg aactcgagca ccaccaccac   1380
caccactga                                                            1389
```

<210> SEQ ID NO 7
<211> LENGTH: 324
<212> TYPE: PRT
<213> ORGANISM: Synechocystis PCC6803
<220> FEATURE:
<221> NAME/KEY: PEPTIDE
<222> LOCATION: (1)..(324)
<223> OTHER INFORMATION: carbonic anhydrase (cytoplasmic expression)

<400> SEQUENCE: 7

```
Met Ala Glu Val Ser Leu Ile Ser Gln Thr Asn Cys Pro Ala Val Leu
 1               5                  10                  15

Asp Pro Pro Gln Val Phe Asn Asp Thr Met Glu Gly Trp Asn Ser
            20                  25                  30

Ile Asn Gly Asp Arg Met Gln Arg Leu Ile Glu Gly Leu Gln Lys Phe
        35                  40                  45

Arg Glu Gly Tyr Phe Ser Ser His Arg Asp Leu Phe Glu Gln Leu Ser
    50                  55                  60

His Gly Gln His Pro Arg Ile Leu Phe Ile Cys Cys Ser Asp Ser Arg
65                  70                  75                  80

Val Asp Pro Asn Leu Ile Thr Gln Ser Glu Val Gly Asp Leu Phe Val
                85                  90                  95

Ile Arg Asn Ala Gly Asn Ile Ile Pro Pro Tyr Gly Ala Ala Asn Gly
            100                 105                 110

Gly Glu Gly Ala Ala Met Glu Tyr Ala Leu Val Ala Leu Glu Ile Asn
        115                 120                 125

Gln Ile Ile Val Cys Gly His Ser His Cys Gly Ala Met Lys Gly Leu
    130                 135                 140

Leu Lys Leu Asn Ser Leu Gln Glu Lys Leu Pro Leu Val Tyr Asp Trp
145                 150                 155                 160

Leu Lys His Thr Glu Ala Thr Arg Arg Leu Val Leu Asp Asn Tyr Ser
                165                 170                 175

His Leu Glu Gly Glu Asp Leu Ile Glu Val Ala Val Ala Glu Asn Ile
            180                 185                 190

Leu Thr Gln Leu Lys Asn Leu Gln Thr Tyr Pro Ala Ile His Ser Arg
        195                 200                 205

Leu His Arg Gly Asp Leu Ser Leu His Gly Trp Ile Tyr Arg Ile Glu
    210                 215                 220

Glu Gly Glu Val Leu Ala Tyr Asp Gly Val Leu His Asp Phe Val Ala
225                 230                 235                 240

Pro Gln Ser Arg Ile Asn Ala Leu Glu Pro Glu Asp Glu Tyr Ala Pro
                245                 250                 255

His Pro Asn Ser Pro Leu Ile Ser Tyr Asp Ala Phe Lys Val Pro Gly
            260                 265                 270

Lys Glu Arg Pro Gly Arg Glu Lys Ala Thr Glu Ser Pro Ala Pro Gln
        275                 280                 285

Leu Ser Pro Leu Pro Gly Phe Gly His Leu Pro Arg Glu Gln Ala Glu
    290                 295                 300
```

Arg Ile Tyr Arg Gly Ser Arg Lys Leu Ala Ala Ala Leu Glu His His
305                 310                 315                 320

His His His His

<210> SEQ ID NO 8
<211> LENGTH: 975
<212> TYPE: DNA
<213> ORGANISM: Synechocystis PCC6803
<220> FEATURE:
<221> NAME/KEY: gene
<222> LOCATION: (1)..(975)
<223> OTHER INFORMATION: carbonic anhydrase (cytoplasmic expression)

<400> SEQUENCE: 8

```
atggccgaag tttcattgat atcccagaca aattgccccg ctgtcctaga cccccccgccg    60
caagtcttca tgatacaat ggaaggctgg aattccatca acggcgatcg tatgcaaaga    120
ctcatcgagg gactacaaaa atttcgagaa ggttatttct cttcccaccg tgacctcttt    180
gagcaacttt ctcacggcca acatccccgc attctcttca tctgttgttc cgattcccgg    240
gtggacccca atttaatcac ccaatcggaa gtgggcgacc tgtttgttat tcgcaacgct    300
ggcaatatta ttcccccta tggagcagcc aacggtgggg aaggggcagc catggaatat    360
gccctagtgg cgctggaaat taatcagatc atcgtctgtg ccattcccca ctgcggagcc    420
atgaaaggtc tgctcaaact caactctctc caggaaaaac ttcctctggt gtacgattgg    480
ctcaaacata cggaagccac ccgccgtcta gttctagaca attacagcca tctggaaggg    540
gaagatttga ttgaagttgc tgtggcagaa aatattctca cccaactcaa aaacctccag    600
acctatcccg ccatccattc ccggttacat cggggagacc tttccctcca cggctggatt    660
tatcgcattg aagagggtga agtactggcc tacgacggtg tactccatga ttttgtcgcc    720
ccccaaagtc gcatcaatgc cctggagccg gaggatgagt acgctcccca tcccaactca    780
cccctgattt cctacgatgc gtttaaggtt cccggcaagg aacgtcctgg tcgtgagaaa    840
gcaacagaat ccccagctcc ccaactgtct cctttacctg gttttggcca tttgcccagg    900
gaacaggcgg agcgcattta tcgaggctcc cgtaagcttg cggccgcact cgagcaccac    960
caccaccacc actga                                                    975
```

<210> SEQ ID NO 9
<211> LENGTH: 368
<212> TYPE: PRT
<213> ORGANISM: Synechocystis PCC6803
<220> FEATURE:
<221> NAME/KEY: PEPTIDE
<222> LOCATION: (1)..(368)
<223> OTHER INFORMATION: carbonic anhydrase (periplasmic expression)

<400> SEQUENCE: 9

Met Asn Asn Asn Asp Leu Phe Gln Ala Ser Arg Arg Phe Leu Ala
1               5                   10                  15

Gln Leu Gly Gly Leu Thr Val Ala Gly Met Leu Gly Pro Ser Leu Leu
                20                  25                  30

Thr Pro Arg Arg Ala Thr Ala Ala Gln Ala Ala Met Gly Ala Glu Val
            35                  40                  45

Ser Leu Ile Ser Gln Thr Asn Cys Pro Ala Val Leu Asp Pro Pro
        50                  55                  60

Gln Val Phe Asn Asp Thr Met Glu Gly Trp Asn Ser Ile Asn Gly Asp
65                  70                  75                  80

```
Arg Met Gln Arg Leu Ile Glu Gly Leu Gln Lys Phe Arg Glu Gly Tyr
             85                  90                  95

Phe Ser Ser His Arg Asp Leu Phe Glu Gln Leu Ser His Gly Gln His
         100                 105                 110

Pro Arg Ile Leu Phe Ile Cys Cys Ser Asp Ser Arg Val Asp Pro Asn
     115                 120                 125

Leu Ile Thr Gln Ser Glu Val Gly Asp Leu Phe Val Ile Arg Asn Ala
 130                 135                 140

Gly Asn Ile Ile Pro Pro Tyr Gly Ala Ala Asn Gly Gly Glu Gly Ala
145                 150                 155                 160

Ala Met Glu Tyr Ala Leu Val Ala Leu Glu Ile Asn Gln Ile Ile Val
             165                 170                 175

Cys Gly His Ser His Cys Gly Ala Met Lys Gly Leu Leu Lys Leu Asn
         180                 185                 190

Ser Leu Gln Glu Lys Leu Pro Leu Val Tyr Asp Trp Leu Lys His Thr
     195                 200                 205

Glu Ala Thr Arg Arg Leu Val Leu Asp Asn Tyr Ser His Leu Glu Gly
 210                 215                 220

Glu Asp Leu Ile Glu Val Ala Val Ala Glu Asn Ile Leu Thr Gln Leu
225                 230                 235                 240

Lys Asn Leu Gln Thr Tyr Pro Ala Ile His Ser Arg Leu His Arg Gly
             245                 250                 255

Asp Leu Ser Leu His Gly Trp Ile Tyr Arg Ile Glu Glu Gly Glu Val
         260                 265                 270

Leu Ala Tyr Asp Gly Val Leu His Asp Phe Val Ala Pro Gln Ser Arg
     275                 280                 285

Ile Asn Ala Leu Glu Pro Glu Asp Glu Tyr Ala Pro His Pro Asn Ser
 290                 295                 300

Pro Leu Ile Ser Tyr Asp Ala Phe Lys Val Pro Gly Lys Glu Arg Pro
305                 310                 315                 320

Gly Arg Glu Lys Ala Thr Glu Ser Pro Ala Pro Gln Leu Ser Pro Leu
             325                 330                 335

Pro Gly Phe Gly His Leu Pro Arg Glu Gln Ala Glu Arg Ile Tyr Arg
         340                 345                 350

Gly Ser Arg Lys Leu Ala Ala Ala Leu Glu His His His His His His
     355                 360                 365

<210> SEQ ID NO 10
<211> LENGTH: 1107
<212> TYPE: DNA
<213> ORGANISM: Synechocystis PCC6803
<220> FEATURE:
<221> NAME/KEY: gene
<222> LOCATION: (1)..(1107)
<223> OTHER INFORMATION: carbonic anhydrase (periplasmic expression)

<400> SEQUENCE: 10
atgaacaata acgatctctt tcaggcatca cgtcggcgtt ttctggcaca actcggcggc      60
ttaaccgtcg ccgggatgct ggggccgtca ttgttaacgc cgcgacgtgc gactgcggcg     120
caagcggcca tgggagccga agtttcattg atatcccaga caaattgccc cgctgtccta     180
gaccccccgc cgcaagtctt caatgataca atggaaggct ggaattccat caacggcgat     240
cgtatgcaaa gactcatcga gggactacaa aaatttcgag aaggttattt ctcttcccac     300
cgtgacctct tgagcaact tctcacggc aacatcccc gcattctctt catctgttgt        360
tccgattccc gggtggaccc caatttaatc acccaatcgg aagtgggcga cctgttttgt     420
```

```
attcgcaacg ctggcaatat tattcccccc tatggagcag ccaacggtgg ggaaggggca    480
gccatggaat atgccctagt ggcgctggaa attaatcaga tcatcgtctg tggccattcc    540
cactgcggag ccatgaaagg tctgctcaaa ctcaactctc tccaggaaaa acttcctctg    600
gtgtacgatt ggctcaaaca tacggaagcc acccgccgtc tagttctaga caattacagc    660
catctggaag gggaagattt gattgaagtt gctgtggcag aaaatattct cacccaactc    720
aaaaacctcc agacctatcc cgccatccat tcccggttac atcggggaga cctttccctc    780
cacggctgga tttatcgcat tgaagagggt gaagtactgg cctacgacgg tgtactccat    840
gattttgtcg cccccaaag tcgcatcaat gccctggagc cggaggatga gtacgctccc    900
catcccaact caccctgat ttcctacgat gcgtttaagg ttcccggcaa ggaacgtcct    960
ggtcgtgaga aagcaacaga atccccagct ccccaactgt ctcctttacc tggttttggc   1020
catttgccca gggaacaggc ggagcgcatt tatcgaggct cccgtaagct tgcggccgca   1080
ctcgagcacc accaccacca ccactga                                       1107
```

<210> SEQ ID NO 11
<211> LENGTH: 231
<212> TYPE: PRT
<213> ORGANISM: Escherichia coli
<220> FEATURE:
<221> NAME/KEY: PEPTIDE
<222> LOCATION: (1)..(231)
<223> OTHER INFORMATION: carbonic anhydrase (cytoplasmic expression)

<400> SEQUENCE: 11

```
Met Lys Glu Ile Ile Asp Gly Phe Leu Lys Phe Gln Arg Glu Ala Phe
 1               5                  10                  15

Pro Lys Arg Glu Ala Leu Phe Lys Gln Leu Ala Thr Gln Gln Ser Pro
             20                  25                  30

Arg Thr Leu Phe Ile Ser Cys Ser Asp Ser Arg Leu Val Pro Glu Leu
         35                  40                  45

Val Thr Gln Arg Glu Pro Gly Asp Leu Phe Val Ile Arg Asn Ala Gly
     50                  55                  60

Asn Ile Val Pro Ser Tyr Gly Pro Glu Pro Gly Gly Val Ser Ala Ser
 65                  70                  75                  80

Val Glu Tyr Ala Val Ala Ala Leu Arg Val Ser Asp Ile Val Ile Cys
                 85                  90                  95

Gly His Ser Asn Cys Gly Ala Met Thr Ala Ile Ala Ser Cys Gln Cys
            100                 105                 110

Met Asp His Met Pro Ala Val Ser His Trp Leu Arg Tyr Ala Asp Ser
        115                 120                 125

Ala Arg Val Val Asn Glu Ala Arg Pro His Ser Asp Leu Pro Ser Lys
    130                 135                 140

Ala Ala Met Val Arg Glu Asn Val Ile Ala Gln Leu Ala Asn Leu
145                 150                 155                 160

Gln Thr His Pro Ser Val Arg Leu Ala Leu Glu Glu Gly Gly Ser Leu
                165                 170                 175

His Gly Trp Val Tyr Asp Ile Glu Ser Gly Ser Ile Ala Ala Phe Asp
            180                 185                 190

Gly Ala Thr Arg Gln Phe Val Pro Leu Ala Ala Asn Pro Arg Val Cys
        195                 200                 205

Ala Ile Arg Leu Arg Gln Pro Thr Ala Ala Lys Leu Ala Ala Ala Leu
    210                 215                 220
```

Glu His His His His His His
225             230

<210> SEQ ID NO 12
<211> LENGTH: 696
<212> TYPE: DNA
<213> ORGANISM: Escherichia coli
<220> FEATURE:
<221> NAME/KEY: gene
<222> LOCATION: (1)..(696)
<223> OTHER INFORMATION: carbonic anhydrase (cytoplasmic expression)

<400> SEQUENCE: 12

```
atgaaagaga ttattgatgg attccttaaa ttccagcgcg aggcatttcc gaagcgggaa      60
gccttgttta aacagctggc gacacagcaa agcccgcgca cacttttttat ctcctgctcc    120
gacagccgtc tggtccctga gctggtgacg caacgtgagc ctggcgatct gttcgttatt    180
cgcaacgcgg gcaatatcgt cccttcctac gggccggaac ccggtggcgt ttctgcttcg    240
gtggagtatg ccgtcgctgc gcttcgggta tctgacattg tgatttgtgg tcattccaac    300
tgtggcgcga tgaccgccat tgccagctgt cagtgcatgg accatatgcc tgccgtctcc    360
cactggctgc gttatgccga ttcagcccgc gtcgttaatg aggcgcgccc gcattccgat    420
ttaccgtcaa agctgcggc gatggtacgt gaaaacgtca ttgctcagtt ggctaatttg    480
caaactcatc catcggtgcg cctggcgctc gaagagggcg atcgctgca cggctgggtc    540
tacgacattg aaagcggcag catcgcagct tttgacggcg caacccgcca gtttgtgcca    600
ctggccgcta atcctcgcgt ttgtgccata cgcctacgcc aaccgaccgc agcgaagctt    660
gcggccgcac tcgagcacca ccaccaccac cactga                              696
```

<210> SEQ ID NO 13
<211> LENGTH: 275
<212> TYPE: PRT
<213> ORGANISM: Escherichia coli
<220> FEATURE:
<221> NAME/KEY: PEPTIDE
<222> LOCATION: (1)..(275)
<223> OTHER INFORMATION: carbonic anhydrase (periplasmic expression)

<400> SEQUENCE: 13

Met Asn Asn Asn Asp Leu Phe Gln Ala Ser Arg Arg Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Thr Ala Ala Gln Ala Ala Met Gly Lys Glu Ile
        35                  40                  45

Ile Asp Gly Phe Leu Lys Phe Gln Arg Glu Ala Phe Pro Lys Arg Glu
    50                  55                  60

Ala Leu Phe Lys Gln Leu Ala Thr Gln Gln Ser Pro Arg Thr Leu Phe
65                  70                  75                  80

Ile Ser Cys Ser Asp Ser Arg Leu Val Pro Glu Leu Val Thr Gln Arg
                85                  90                  95

Glu Pro Gly Asp Leu Phe Val Ile Arg Asn Ala Gly Asn Ile Val Pro
            100                 105                 110

Ser Tyr Gly Pro Glu Pro Gly Gly Val Ser Ala Ser Val Glu Tyr Ala
        115                 120                 125

Val Ala Ala Leu Arg Val Ser Asp Ile Val Ile Cys Gly His Ser Asn
    130                 135                 140

```
Cys Gly Ala Met Thr Ala Ile Ala Ser Cys Gln Cys Met Asp His Met
145                 150                 155                 160

Pro Ala Val Ser His Trp Leu Arg Tyr Ala Asp Ser Ala Arg Val Val
                165                 170                 175

Asn Glu Ala Arg Pro His Ser Asp Leu Pro Ser Lys Ala Ala Ala Met
            180                 185                 190

Val Arg Glu Asn Val Ile Ala Gln Leu Ala Asn Leu Gln Thr His Pro
        195                 200                 205

Ser Val Arg Leu Ala Leu Glu Glu Gly Gly Ser Leu His Gly Trp Val
    210                 215                 220

Tyr Asp Ile Glu Ser Gly Ser Ile Ala Ala Phe Asp Gly Ala Thr Arg
225                 230                 235                 240

Gln Phe Val Pro Leu Ala Ala Asn Pro Arg Val Cys Ala Ile Arg Leu
                245                 250                 255

Arg Gln Pro Thr Ala Ala Lys Leu Ala Ala Ala Leu Glu His His His
            260                 265                 270

His His His
        275

<210> SEQ ID NO 14
<211> LENGTH: 828
<212> TYPE: DNA
<213> ORGANISM: Escherichia coli
<220> FEATURE:
<221> NAME/KEY: gene
<222> LOCATION: (1)..(828)
<223> OTHER INFORMATION: carbonic anhydrase (periplasmic expression)

<400> SEQUENCE: 14
atgaacaata acgatctctt tcaggcatca cgtcggcgtt ttctggcaca actcggcggc      60
ttaaccgtcg ccgggatgct ggggccgtca ttgttaacgc cgcgacgtgc gactgcggcg     120
caagcggcca tgggaaaaga gattattgat ggattcctta aattccagcg cgaggcattt     180
ccgaagcggg aagccttgtt taaacagctg gcgacacagc aaagcccgcg cacactttt      240 atctcctgct ccgacagccg tctggtccct gagctggtga cgcaacgtga gcctggcgat     300
ctgttcgtta ttcgcaacgc gggcaatatc gtcccttcct acgggccgga acccggtggc     360
gtttctgctt cggtggagta tgccgtcgct gcgcttcggg tatctgacat tgtgatttgt     420
ggtcattcca actgtggcgc gatgaccgcc attgccagct gtcagtgcat ggaccatatg     480
cctgccgtct cccactggct gcgttatgcc gattcagccc gcgtcgttaa tgaggcgcgc     540
ccgcattccg atttaccgtc aaaagctgcg gcgatggtac gtgaaaacgt cattgctcag     600
ttggctaatt tgcaaactca tccatcggtg cgcctggcgc tcgaagaggg cggatcgctg     660
cacggctggg tctacgacat tgaaagcggc agcatcgcag cttttgacgg cgcaacccgc     720
cagtttgtgc cactggccgc taatcctcgc gtttgtgcca tacgcctacg ccaaccgacc     780
gcagcgaagc ttgcggccgc actcgagcac caccaccacc accactga                 828

<210> SEQ ID NO 15
<211> LENGTH: 21
<212> TYPE: DNA
<213> ORGANISM: Artificial Sequence
<220> FEATURE:
<223> OTHER INFORMATION: Forward (No signal) : NCA-C-FP

<400> SEQUENCE: 15
catatgcacg gcaatcacac c                                                21
```

```
<210> SEQ ID NO 16
<211> LENGTH: 27
<212> TYPE: DNA
<213> ORGANISM: Artificial Sequence
<220> FEATURE:
<223> OTHER INFORMATION: Common reverse : NCA-BP

<400> SEQUENCE: 16
aagcttttca ataactacac gtgcatt                                              27

<210> SEQ ID NO 17
<211> LENGTH: 27
<212> TYPE: DNA
<213> ORGANISM: Artificial Sequence
<220> FEATURE:
<223> OTHER INFORMATION: Forward (No signal) : SCA-C-FP

<400> SEQUENCE: 17
catatggccg aagtttcatt gatatcc                                              27

<210> SEQ ID NO 18
<211> LENGTH: 29
<212> TYPE: DNA
<213> ORGANISM: Artificial Sequence
<220> FEATURE:
<223> OTHER INFORMATION: Common reverse : SCA-BP

<400> SEQUENCE: 18
caagcttacg ggagcctcga taaatgcgc                                            29

<210> SEQ ID NO 19
<211> LENGTH: 28
<212> TYPE: DNA
<213> ORGANISM: Artificial Sequence
<220> FEATURE:
<223> OTHER INFORMATION: Forward (No signal) : ECA-C-FP

<400> SEQUENCE: 19
catatgaaag agattattga tggattcc                                             28

<210> SEQ ID NO 20
<211> LENGTH: 28
<212> TYPE: DNA
<213> ORGANISM: Artificial Sequence
<220> FEATURE:
<223> OTHER INFORMATION: Common reverse : ECA-BP

<400> SEQUENCE: 20
caagcttcgc tgcggtcggt tggcgtag                                             28

<210> SEQ ID NO 21
<211> LENGTH: 23
<212> TYPE: DNA
<213> ORGANISM: Artificial Sequence
<220> FEATURE:
<223> OTHER INFORMATION: Forward (Signal): NCA-T-FP

<400> SEQUENCE: 21
ccatgggaca cggcaatcac acc                                                  23

<210> SEQ ID NO 22
<211> LENGTH: 29
<212> TYPE: DNA
<213> ORGANISM: Artificial Sequence
<220> FEATURE:
<223> OTHER INFORMATION: Forward (Signal) : SCA-T-FP
```

```
<400> SEQUENCE: 22
ccatgggagc cgaagtttca ttgatatcc                                          29

<210> SEQ ID NO 23
<211> LENGTH: 27
<212> TYPE: DNA
<213> ORGANISM: Artificial Sequence
<220> FEATURE:
<223> OTHER INFORMATION: Forward (Signal) : ECA-T-FP

<400> SEQUENCE: 23
ccatgggaaa agattattga tggattc                                            27

<210> SEQ ID NO 24
<211> LENGTH: 27
<212> TYPE: DNA
<213> ORGANISM: Artificial Sequence
<220> FEATURE:
<223> OTHER INFORMATION: Forward (signal) : NCA-INPNC-FP

<400> SEQUENCE: 24
agatctcacg gcaatcacac ccattgg                                            27

<210> SEQ ID NO 25
<211> LENGTH: 27
<212> TYPE: DNA
<213> ORGANISM: Artificial Sequence
<220> FEATURE:
<223> OTHER INFORMATION: Reverse : NCA-INPNC-BP

<400> SEQUENCE: 25
aagctttcag tggtggtggt ggtggtg                                            27
```